US007351693B2

(12) United States Patent
Secombes et al.

(10) Patent No.: US 7,351,693 B2
(45) Date of Patent: Apr. 1, 2008

(54) PEPTIDES AND NUCLEIC ACIDS OF THE CATHELICIDIN FAMILY, DERIVED FROM FISH, AND USES THEREOF

(75) Inventors: Christopher John Secombes, Aberdeen (GB); Olga Pleguezuelos, London (GB)

(73) Assignee: University Court of the University of Aberdeen, Aberden, Aberdeenshire (GB)

( * ) Notice: Subject to any disclaimer, the term of this patent is extended or adjusted under 35 U.S.C. 154(b) by 66 days.

(21) Appl. No.: 10/502,617

(22) PCT Filed: Jan. 27, 2003

(86) PCT No.: PCT/GB03/00322

§ 371 (c)(1),
(2), (4) Date: Mar. 16, 2005

(87) PCT Pub. No.: WO03/062271

PCT Pub. Date: Jul. 31, 2003

(65) Prior Publication Data
US 2006/0189538 A1 Aug. 24, 2006

(30) Foreign Application Priority Data
Jan. 25, 2002 (GB) .................................. 0201744.0
Jun. 25, 2002 (GB) .................................. 0214660.3

(51) Int. Cl.
*A61K 38/17* (2006.01)
*A61P 31/04* (2006.01)
*C07K 14/46* (2006.01)
*C12N 15/10* (2006.01)

(52) U.S. Cl. .......................... 514/11; 119/231; 514/12; 514/13; 514/15; 514/21; 530/324; 530/326; 530/328; 530/857

(58) Field of Classification Search ................. None
See application file for complete search history.

(56) References Cited

U.S. PATENT DOCUMENTS 6,172,185 B1    1/2001  Hancock
2007/0020624 A1*  1/2007  Rubenfield et al. ............ 435/6

FOREIGN PATENT DOCUMENTS

EP        0 665 239 A1    8/1995
WO        01/12668        2/2001

OTHER PUBLICATIONS

Chen, J., et al., "Development of Protegrins for the Treatment and Prevention of Oral Mucositis: Structure-Activity Relationships of Synthetic Protegrin Analogues," Biopolymers (Peptide Science) 55: 88-98 (2000).
Larrick, J.W., et al., "A Novel Granulocyte-Derived Peptide with Lipopolysaccharide-Neutralizing Acitivity," Journal of Immunology, 152: 231-241, (1994).

Niyonsaba, F., et al, "Evaluation of the effects of peptide antibiotics human β-defensins-1/-2 and LL-37 on histamine release and prostaglandin $D_2$ production from mast cells," European Journal of Immunology, 31: 1066-1075 (2001).
Lillard, JR., J.W., et al., "Mechanisms for induction of acquired host immunity by neutrophil peptide defensins," Proc. Natl. Acad. Sci., USA, 96: 651-656 (1999).
Gallo, R.L., et al., "Syndecans, cell surface heparan sulfate proteoglycans, are induced by a proline-rich antimicrobial peptide from wounds," Proc. Natl. Acad. Sci. USA, 91: 11035-11039 (1994).
Zhang, G., et al., "Porcine antimicrobial peptides: New prospects for ancient molecules of host defense," Vet. Res. 31: 277-296 (2000).
Gennaro, R., et al., "Structural Features and Biological Activites of the Cathelicidin-Derived Antimicrobial Peptides," Biopolymers 55:31-49 (2000).
Frank, R.W., et al., "Amino Acid Sequences of Two Proline-rich Bactenecins," The Journal of Biological Chemistry, 265: 18871-18874 (1990).
Harwig, S.S.L., et al., "Prophenin-1, an exceptionally proline-rich antimicrobial peptide from porcine leukocytes," FEBS Letters 362: 65-69 (1995).
Gennaro, R., et al., "Biological characterization of a novel mammalian antimicrobial peptide," Biochimica et Biophysica Acta, 1425: 361-368 (1998).
Gennaro, R., et al., "Purification, Composition, and Activity of Two Bactenecins, Antibacterial Peptides of Bovine Neutrophils," Infection and Immunity, 57: 3142-3146, (1989).
Niyonsaba, F., et al. "Evaluation of the effects of peptide antibiotics human beta-defensins-1/-2 and LL37 on histamine release and prostaglandin $D_2$ production from mast cells." European Journal of Immunology, vol. 31. 2001. pp. 1066-1075.
Risso, A. "Leukocyte antimicrobial peptides: multifunctional effector molecules of innate immunity." Journal of Leukocyte Biology, vol. 68. Dec. 2000. pp. 785-792.
Yang, D., et al. "Participation of mammalian defensins and cathelicidins in antimicrobial immunity: receptors and activities of human defensins and cathelicidin." Journal of Leukocyte Biology, vol. 69. May 2001. pp. 691-697.
Chen, J., et al. "Development of Protegrins for the Treatment of Precention of Oral Mucositis: Structure-Activity Relationship of Synthetic Protegrin Analogues." Biopolymers (Peptide Science) vol. 55. Jul. 28, 2000. pp. 88-98.
Larrick, J.W., et al. "A Novel Granulocyte-Derived Peptide with Lipopolysaccharide-Neutralizing Activity." Journal of Immunology, vol. 152. American Association of Immunologists. Oct. 4, 1994. pp. 231-240.
Lillard, JR., J.W., et al. "Mechanisms for induction of acquired host immunity by neutrophil peptide defensins." Proc. Natl. Acad. Sci., vol. 96. 1999. pp. 651-656.

(Continued)

*Primary Examiner*—Jeffrey Edwin Russel
(74) *Attorney, Agent, or Firm*—Dann, Dorfman, Herrell & Skillman, P.C.; Kathleen D. Rigaut

(57) ABSTRACT

The invention relates to anti-microbial and immunostimulatory molecules of the cathelicidin family derived from fish. The invention provides a novel cathelicidin molecule, fragments, derivatives and uses thereof, and nucleic acids encoding the same.

27 Claims, 9 Drawing Sheets

OTHER PUBLICATIONS

Gallo, R., et al. "Syndecans, cell surface heparan sulfate proteoglycans, are induced by a proline-rich antimicrobial peptide from wounds." Proc. Natl. Acad. Sci., vol. 91. Nov. 1994. pp. 11035-11039.

Zhang, G., et al. "Procine antimicrobial peptides: New prospects for ancient molecules of host defense." Vet. Res., vol. 31. 2000. pp. 277-296.

Gennaro, R., et al. "Structural Features and Biological Activities of the Cathelicidin-Derived Antimicrobial Peptides." Biopolymers (Peptide Science), vol. 55. 2000. pp. 31-49.

Frank, R.W., et al. "Amino Acid Sequences of Two Proline-rich Bactenecins." Journal of Biological Chemistry, vol. 265, No. 31. American Society for Biochemistry and Molecular Biology, Enc. Nov. 5, 1990. pp. 18871-18874.

Harwig, S.S.L., et al. "Prophenin-1, an exceptionally proline-rich antimicrobial peptide from porcine leukocytes." FEBS Letters 362: 65-69 (1995).

Gennaro, R., et al. "Biological characterization of a novel mammalian antimicrobial peptide." Biochimica et Biophysica Acta, vol. 1425. Aug. 4, 1998. pp. 361-368.

Gennaro, R., et al. "Purification, Composition, and Activity of Two Bactenecins, Antibacterial Peptides of Bovine Neutrophils." Infection and Immunity, vol. 57, No. 10. American Society for Microbiology. Oct. 1989. pp. 3142-3146.

EMBL Online! SL1-0434 Atlantic Salmon liver Salmo salar cDNA clone SL1-0434, mRNA sequence, Oct. 4, 2001. Douglas, S.E., et al. "Expressed sequence tags. A snapshot of the fish genome." Database acession No. BG935125.

EMBL Online! cDNA library Salmo salar cDNA clone MEN-1087, Feb. 3, 2001.

Davey, G.C., et al. "A survey of genes in the Atlantic salmon (Salmo salar) as identified by expressed sequence tags." GENE, vol. 263. Elsevier Science Publishers: Amsterdam, Netherlands. Jan. 2001. pp. 121-130.

Shinnar, A.E., et al. Antimicrobial peptides from hagfish: Ancient member of cathelicidin gene family contains bromotryptophan. FASEB Journal, vol. 13, No. 7. Apr. 23, 1999. p. A1395.

Basanez, G., et al. "Interaction of hagfish cathelicidin antimicrobial peptides with model lipid membranes." FEBS Letters, vol. 532, No. 1-2. Elsevier Science Publishers: Amsterdam, Netherlands. Dec. 4, 2002. pp. 115-120.

Tossi, A., al al. "Design of synthetic antimicrobial peptides based on sequence analogy and amphipathicity." European Journal of Biochemistry, vol. 250, No. 2. Berlin, Germany. Dec. 1997. pp. 549-558.

Tossi, A., et al. "Amphipathic Alpha-Helical Antimicrobial Peptides." Biopolymers (Peptide Science), vol. 55, No. 1. 2000. pp. 4-30.

Epand, R.M., et al. "Diversity of antimicrobial peptides and their mechanisms of action." Biochimica et Biophysica Acta, vol. 1462, No. 1-2. Elsevier Science Publishers: Amsterdam, Netherlands. Dec. 15, 1999. pp. 11-28.

Gallo, R., et al. "Antimicrobial peptides: An Emerging Concept in Cutaneous Biology." Journal of Investigative Dermatology, vol. 111, No. 5. Society for Investigative Dermatology, USA. Nov. 1998. pp. 739-743.

Zanetti, M., et al. "Cathelicidins: a novel protein family with a common proregion and a variable C-terminal antimicrobial domain." FEBS Letters, vol. 374, No. 1. Amsterdam, Netherlands. Oct. 23, 1995. pp. 1-5.

* cited by examiner

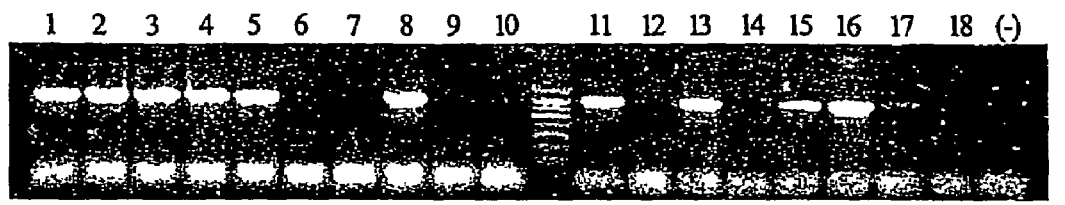
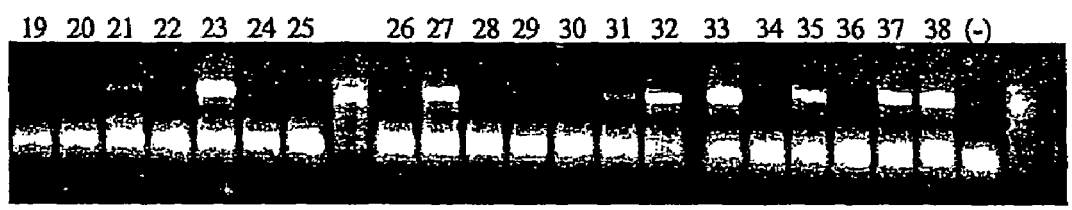
Figure 3
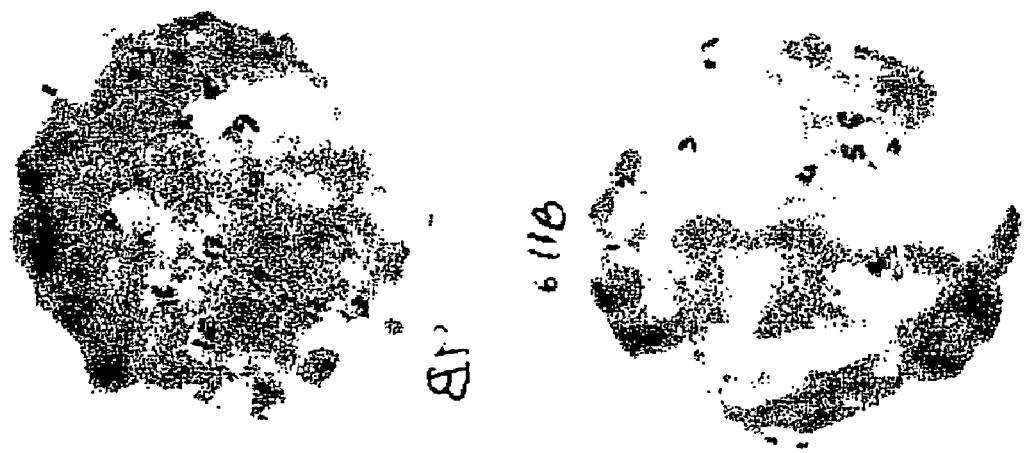
Figure 4

```
1   ATGTGAAGGTCCAGGTGAGATCTCTCATCCTGCTCGCTGTGGCTGTCCTG
     V  K  V  Q  V  R  S  L  I  L  L  A  V  A  V  L

51  CAGGTCAGATCTCAGAACCAGACTGAGACCAGATATGAAGACATCATCTT
     Q  V  R  S  Q  N  Q  T  E  T  R  Y  E  D  I  I  L

101 AGTTGCTTTGCCTCAGCTGCTTCCTGGGGAAGAGCAGGCTTTCCGTCCAA
     V  A  L  P  Q  L  L  P  G  E  E  Q  A  F  R  P

151 TTCTGAACCAGCTCCAAGTCGAGACTTTAAATACAGAGGATGTGGACCAG
     I  L  N  Q  L  Q  V  E  T  L  N  T  E  D  V  D  Q

201 TCTGAGGTGTCTGTAAGGCTGACCTTCCCCATACAGGAGACTTTCTGTAG
     S  E  V  S  V  R  L  T  F  P  I  Q  E  T  F  C  S

251 TAAATCACAGGGGCAGCCAGGCAAACCATGCCCTCTGAAGAAAAATGGGA
     K  S  Q  G  Q  P  G  K  P  C  P  L  K  K  N  G

301 AACTAATGATGTGCAGCATGAAAGTCAGACATCCGATTCTGGAGGCAAGC
     K  L  M  M  C  S  M  K  V  R  H  P  I  L  E  A  S

351 AACAACCTGAACACTGACCTGTCTACATTTGTTTGTGAATACATGGACGC
     N  N  L  N  T  D  L  S  T  F  V  C  E  Y  M  D  A

401 AGAAGATGCTTTGCAGCAGAAGATTCGGACAAGAAGAAGCAAAGTCAGAA
     E  D  A  L  Q  Q  K  I  R  T  R  R  S  K  V  R

451 TATGCTCCAGAGACAAAAATTGTGTCTCTCGTCCTGGGGTTGGCTCCATA
     I  C  S  R  D  K  N  C  V  S  R  P  G  V  G  S  I

501 ATTGGTCGTCCTGGGGGTGGCTCCTTAATTGGTCGTCCTGGGGGTGGCTC
     I  G  R  P  G  G  G  S  L  I  G  R  P  G  G  G  S

551 CGTAATTGGTCGTCCTGGGGGTGGCTCTCCTCCTGGGGGTGGCTCTTTCA
     V  I  G  R  P  G  G  G  S  P  P  G  G  G  S  F

601 ATGATGAATTTATCAGAGATCACAGTGATGGAAATCGCTTTGCATAGATC
     N  D  E  F  I  R  D  H  S  D  G  N  R  F  A  *

651 AGCACGCTACAACCTCTGGATAACTGCAAAGAACCCATCTATCAAAGAAA

701 TGTCATAAGGTTATTGATCTTTTTTTTTGTATCAACTCTTACATGCCAAT

751 TGTTGCATATTATGAAAATGACTTCTAGATTATGTTTACGCCAATAAACT

801 GCAAAATAAGTTTACAAAAAAAAAAAAAAAAAAA
```

Figure 8

```
31-  PR-39      YREAVLRAVDRLN***E       PR-39      FTVKETVCPRPTRQPPEL CDFKE  -43
32-  CATHELIN   -K-----------***-       CATHELIN   ------------------ L------ -43
33-  FALL-39    -K------I-GI-***Q       FALL-39    ---------- T-Q-S--D----K  -44
31-  PF2        -------------***-       PF2        -------------- R---L------ -45
31-  PG1        -------------***-       PG1        ------------------ L------ -43
31-  PMAP-23    -------------***-       PMAP-23    ------------------ L------ -43
31-  PMAP-36    -------------***-       PMAP-36    ------------ WR---L------ -46
34-  BAC1B      ---------Q--***-        BAC1B      -R------ S-T-Q----Q------ -47
35-  SMAP-29    --------A-Q--***-       SMAP-29    -R-------- TSQ--A-Q------ -48
36-  BAC7S      ---------GQ--***-       BAC7S      -R-------- MSQ----Q------ -47
36-  BAC11S     ---------GQ--***-       BAC11S     -R-------- M-Q----Q------ -50
36-  BAC6S      ---------GQ--***-       BAC6S      -R-------- M-Q----Q------ -50
37-  BAC5B      ----------QF-***-       BAC5B      -R-------- TSQ--L-Q------ -51
34-  INDOL      ----------Q--***-       INDOL      ---------- TIQ--A-Q------ -56
32-  CATH1      -K-----------***-       CATH1      -M-------- IMK-T--Q------ -53
38-  CRAMP      --D-------DF-***Q       CRAMP      -R------ GKAE--L--Q-A---  -54
39-  CAP-18     ----------AF-***Q       CAP-18     ------ E---T-WKL--Q------ -55
40-  BAC-M      -E-I-D--IEAY-***Q       BAC-M      -RI---- E-TSTQERQ-KD---L- -56
41-  P15A       -E-V-AQ-LQFY-***-       P15A       -RI----- IFTLDRQ-GN-A-R-  -57
42-  TROUT      -EDII-V-LPQ-LPGE-       TROUT      -PIQ--F-SKSQG --GKP-PL-K  -58
```

Figure 9

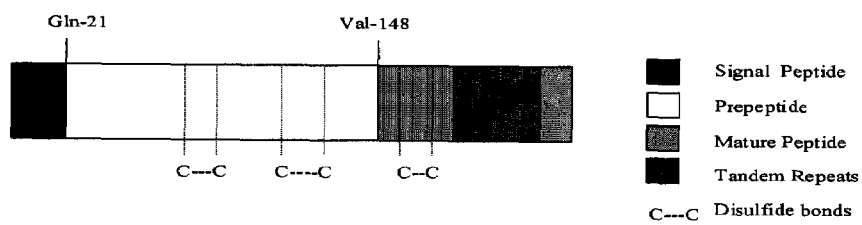

Figure 10

```
59-  PR-39      VRRRPRPPYLPRPRPPPFFPPRLPPRIPPGFPPRFPPRFP GKR
60-  FALL-39    ALLGDFFRKSKEKIGKEFKRIVQRIKDFLRNLVPRTESD
61-  PG1        VRGGRLCYCRRRFCVCVGRG
62-  PMAP-23    VRIIDLLWRVRRPQKPKFVTVWVR
63-  PMAP-36    VGRFRRLRKKTRKRLKKIGKVLKWIPPIVGSIPLGCG
64-  BAC1B      ARLCRIVVIRVCR
65-  SMAP-29    VRGLRRLGRKIAHGVKKYGPTVLRIIRIAGL
66-  BAC7S      VRRLRPRRPRLPRPRPRPRPRSLPLPRPQPRRIPRPILLPWRPPRPIPRPQPQPIPRWL
67-  BAC6S      VRRLRPRHQHFPSERPWPKPLPLPLPRPGPRPWPKPLPLPLPRPGLRPWPKPL
68-  BAC5B      VRFRPPIRRPPIRPPFYPPFRPPIRPPIFPPIRPPFRPPLGPFPGRRL
69-  TROUT      VRICSRDKNCVSRPGVGSIIGRPGGGSLIGRPGGGSVIGRPGGGSPPGGGSFNDEFIRDHSDGNRFA
```

Figure 11 aaaataagtatatatcgaatttagcaataaagttc tattttggtttcatctgaccatatgacattctctcaatcttcttctggatcatccaaatg ctctctagcaaacttcagacgggtaggccaatgctatgattgatctattgagcagaccaa ttaggctttgttgaaacatgtaggaacatttcaggaaacagattaggccaagttctgtat aaaccatgacgacacttcaggcgggggttccctagaagcctggattgctcaaccctggat ttcattgtaagaacaaaagacagac[tataa]aacagcagaagtaggaagtaggaatcagac
                                         +1

```
  1 ATGAAGATGAAGGTCCAGGTGAGATCTCTCATCCTGCTCGCTGTGGCTGTCCTGCAGGTC  20
    M   K   M   K   V   Q   V   R   S   L   I   L   L   A   V   A   V   L   Q   V

61 AGATCTCAGAACCAGACTGAGACCAGATATGAAGACATCATCT^T_CAGTTGCTTTGCCTCAG  40
    R   S   Q   N   Q   T   E   T   R   Y   E   D   I   I^L_S V   A   L   P   Q

121 CTGCTTCCTGGGGAAGAGCAGGCTTTCCGTCCAATTCTGAACCAGCTCCAAGTCGAGACT  60
    L   L   P   G   E   E   Q   A   F   R   P   I   L   N   Q   L   Q   V   E   T 181 gtgagtattctgacagtatgaatgtgtccttccttcaaaaaaagtttgtgtcatgtttta 241 tttaatattattctttcagtcaagtcaagggataattgtctgtttaatatgcaccatcgt 301 gtacacattttccaagtcctttattgtggaaaagaaacagactcaatgtgggggaatgac 361 aattgaaatgaatgacaatactataagtcgcagtattgtctttgtctctcggaaatcagT 421 TGAATACAGAGGATGTGGACCAGTCTGAGGTGTCTGTAAGGCTGACCTTCCCCATACAGG  80
    L   N   T   E   D   V   D   Q   S   E   V   S   V   R   L   T   F   P   I   Q 481 AGACTTTCTGTAGTAAATCACAGGGGCAGCCAGGCAAACCATGCCCTCTGAAGAAAAATG 100
    E   T   F   C   S   K   S   Q   G   Q   P   G   K   P   C   P   L   K   K   N 541 GGgtaagaacaattggattttacagtattgtgggggaataataatcatgggaagcaggaa
    G 601 atgacaaataatatgctgaggttagcaaatggctaattgtcaattactccttcctctagA 661 AAC^T_GAATGATGTGCAGCATGAA^A_GGTCAGACATCCGATTCTGGAGGCAAGCAACAACCTGA 121
    K  ^L_R M   M   G   S   M   K   V   R   H   P   I   L   E   A   S   N   N   L 721 ACACTGACCTGTCTACATTTGTTTGTGAATACATGGACGCAGAAGATGCTTTGCAGgtac 140
    N   T   D   L   S   T   F   V   C   E   Y   M   D   A   E   D   A   L   Q 781 tgagcaatgcaagtatttgtcaacacccccttaccgacattagttaggatgtcatgataa 841 tggtagcctaacagtgtcagatcagttggtctgcaatctaaaaatgtagatgtggaaagt 901 gcattatctgcttatgaatttaatggagattgaacttcatgttccttgagatagtaaaca 961 tgcaccttattttctgattatacttgtctaattattccgattttcacgcaaaaaaat 1021 gcaatgaatattttcatgattgcagCAGAAGATTCGGACAAGAAGAAGCAAAGTCAGAA 151
                              Q   K   I   R   T   R   R   S   K   V   R 1081 TATGCTCCAGAG^G_ACAAAAATTGTGTCTCTCGTCCTGGGGTTGGCTCCATAATTGGTCGTC 171
     I   C   S   R  ^G_D K   N   G   V   S   R   P   G   V   G   S   I   I   G   R

1141 CTGGGGGTGGCTCCTTAATTGGTCGTCCTGGGGGTGGCTCCGTAATTGGTCGTCCTGGGG 191
```

```
              P  G  G  G  S  L  I  G  R  P  G  G  G  S  V  L  G  R  P  G
1201 GTGGCTCTCCTCCTGGGGGTGGCTCTTTCAATGATGAATTTATCAGAGATCACAGTGATG 211
      G  G  S  P  P  G  G  G  S  F  N  D  E  F  I  R  D  H  S  D

1261 GAAATCGCTTTGCATAGatcagcacgctacaacctagcacgctacaacctctggataact 216
      G  N  R  F  A  *

1321 gcaaagaacccatctatcaaagaaatgtcataaggttattgatctttttttttgtatcaa 1381 ctcttacatgccaattgttgcatattatgaaaatgacttctagattatgtttacgccaat 1441 aaactgcaaaataagtttacaaaaaaaaaaaaaaaaaa
```

Figure 15

SEQUENCE LISTING

<160> NUMBER OF SEQ ID NOS: 85

<210> SEQ ID NO 1
<211> LENGTH: 833
<212> TYPE: DNA
<213> ORGANISM: Salmo gairdneri

<400> SEQUENCE: 1

```
atgtgaaggt ccaggtgaga tctctcatcc tgctcgctgt ggctgtcctg caggtcagat      60
ctcagaacca gactgagacc agatatgaag acatcatctt agttgctttg cctcagctgc     120
ttcctgggga agagcaggct ttccgtccaa ttctgaacca gctccaagtc gagactttaa     180
atacagagga tgtggaccag tctgaggtgt ctgtaaggct gaccttcccc atacaggaga     240
ctttctgtag taaatcacag gggcagccag gcaaaccatg ccctctgaag aaaaatggga     300
aactaatgat gtgcagcatg aaagtcgaca tccgattct ggaggcaagc aacaacctga      360
acactgacct gtctacattt gtttgtgaat acatggacgc agaagatgct ttgcagcaga     420
agattcggac aagaagaagc aaagtcagaa tatgctccag agacaaaaat tgtgtctctc     480
gtcctggggt tggctccata attggtcgtc ctggggtgg ctccttaatt ggtcgtcctg       540
ggggtggctc cgtaattggt cgtcctgggg gtggctctcc tcctgggggt ggctctttca     600
atgatgaatt tatcagagat cacagtgatg aaatcgctt tgcatagatc agcacgctac      660
aacctctgga taactgcaaa gaacccatct atcaaagaaa tgtcataagg ttattgatct     720
tttttttgt atcaactctt acatgccaat tgttgcatat tatgaaaatg acttctagat      780
tatgtttacg ccaataaact gcaaaataag tttacaaaaa aaaaaaaaaa aaa            833
```

<210> SEQ ID NO 2
<211> LENGTH: 214
<212> TYPE: PRT
<213> ORGANISM: Salmo gairdneri

<400> SEQUENCE: 2

```
Val Lys Val Gln Val Arg Ser Leu Ile Leu Leu Ala Val Ala Val Leu
1               5                   10                  15

Gln Val Arg Ser Gln Asn Gln Thr Glu Thr Arg Tyr Glu Asp Ile Ile
            20                  25                  30

Leu Val Ala Leu Pro Gln Leu Leu Pro Gly Glu Glu Gln Ala Phe Arg
        35                  40                  45

Pro Ile Leu Asn Gln Leu Gln Val Glu Thr Leu Asn Thr Glu Asp Val
    50                  55                  60

Asp Gln Ser Glu Val Ser Val Arg Leu Thr Phe Pro Ile Gln Glu Thr
65                  70                  75                  80

Phe Cys Ser Lys Ser Gln Gly Gln Pro Gly Lys Pro Cys Pro Leu Lys
                85                  90                  95

Lys Asn Gly Lys Leu Met Met Cys Ser Met Lys Val Arg His Pro Ile
            100                 105                 110

Leu Glu Ala Ser Asn Asn Leu Asn Thr Asp Leu Ser Thr Phe Val Cys
        115                 120                 125

Glu Tyr Met Asp Ala Glu Asp Ala Leu Gln Gln Lys Ile Arg Thr Arg
    130                 135                 140

Arg Ser Lys Val Arg Ile Cys Ser Arg Asp Lys Asn Cys Val Ser Arg
145                 150                 155                 160

Pro Gly Val Gly Ser Ile Ile Gly Arg Pro Gly Gly Gly Ser Leu Ile
```

```
                    165                 170                 175
Gly Arg Pro Gly Gly Gly Ser Val Ile Gly Arg Pro Gly Gly Ser
            180                 185                 190

Pro Pro Gly Gly Gly Ser Phe Asn Asp Glu Phe Ile Arg Asp His Ser
        195                 200                 205

Asp Gly Asn Arg Phe Ala
    210

<210> SEQ ID NO 3
<211> LENGTH: 384
<212> TYPE: DNA
<213> ORGANISM: Salmo gairdneri

<400> SEQUENCE: 3
cagaaccaga ctgagaccag atatgaagac atcatcttag ttgctttgcc tcagctgctt      60
cctggggaag agcaggcttt ccgtccaatt ctgaaccagc tccaagtcga gactttaaat     120
acagaggatg tggaccagtc tgaggtgtct gtaaggctga ccttccccat acaggagact     180
ttctgtagta aatcacaggg gcagccaggc aaaccatgcc ctctgaagaa aaatgggaaa     240
ctaatgatgt gcagcatgaa agtcagacat ccgattctgg aggcaagcaa caacctgaac     300
actgacctgt ctacatttgt ttgtgaatac atggacgcag aagatgcttt gcagcagaag     360
attcggacaa gaagaagcaa agtc                                             384

<210> SEQ ID NO 4
<211> LENGTH: 128
<212> TYPE: PRT
<213> ORGANISM: Salmo gairdneri

<400> SEQUENCE: 4

Gln Asn Gln Thr Glu Thr Arg Tyr Glu Asp Ile Ile Leu Val Ala Leu
1               5                   10                  15

Pro Gln Leu Leu Pro Gly Glu Glu Gln Ala Phe Arg Pro Ile Leu Asn
            20                  25                  30

Gln Leu Gln Val Glu Thr Leu Asn Thr Glu Asp Val Asp Gln Ser Glu
        35                  40                  45

Val Ser Val Arg Leu Thr Phe Pro Ile Gln Glu Thr Phe Cys Ser Lys
    50                  55                  60

Ser Gln Gly Gln Pro Gly Lys Pro Cys Pro Leu Lys Lys Asn Gly Lys
65                  70                  75                  80

Leu Met Met Cys Ser Met Lys Val Arg His Pro Ile Leu Glu Ala Ser
                85                  90                  95

Asn Asn Leu Asn Thr Asp Leu Ser Thr Phe Val Cys Glu Tyr Met Asp
            100                 105                 110

Ala Glu Asp Ala Leu Gln Gln Lys Ile Arg Thr Arg Arg Ser Lys Val
        115                 120                 125

<210> SEQ ID NO 5
<211> LENGTH: 51
<212> TYPE: DNA
<213> ORGANISM: Salmo gairdneri

<400> SEQUENCE: 5
tatgaagaca tcatcttagt tgctttgcct cagctgcttc ctggggaaga g               51

<210> SEQ ID NO 6
<211> LENGTH: 17
<212> TYPE: PRT
```

<213> ORGANISM: Salmo gairdneri

<400> SEQUENCE: 6

Tyr Glu Asp Ile Ile Leu Val Ala Leu Pro Gln Leu Leu Pro Gly Glu
1               5                   10                  15

Glu

<210> SEQ ID NO 7
<211> LENGTH: 69
<212> TYPE: DNA
<213> ORGANISM: Salmo gairdneri

<400> SEQUENCE: 7
ttccccatac aggagacttt ctgtagtaaa tcacaggggc agccaggcaa accatgccct      60
ctgaagaaa                                                              69

<210> SEQ ID NO 8
<211> LENGTH: 23
<212> TYPE: PRT
<213> ORGANISM: Salmo gairdneri

<400> SEQUENCE: 8

Phe Pro Ile Gln Glu Thr Phe Cys Ser Lys Ser Gln Gly Gln Pro Gly
1               5                   10                  15

Lys Pro Cys Pro Leu Lys Lys
            20

<210> SEQ ID NO 9
<211> LENGTH: 198
<212> TYPE: DNA
<213> ORGANISM: Salmo gairdneri

<400> SEQUENCE: 9
agaatatgct ccagagacaa aaattgtgtc tctcgtcctg gggttggctc cataattggt      60
cgtcctgggg gtggctcctt aattggtcgt cctgggggtg gctccgtaat tggtcgtcct     120
gggggtggct ctcctcctgg gggtggctct tcaatgatg aatttatcag agatcacagt     180
gatggaaatc gctttgca                                                  198

<210> SEQ ID NO 10
<211> LENGTH: 66
<212> TYPE: PRT
<213> ORGANISM: Salmo gairdneri

<400> SEQUENCE: 10

Arg Ile Cys Ser Arg Asp Lys Asn Cys Val Ser Arg Pro Gly Val Gly
1               5                   10                  15

Ser Ile Ile Gly Arg Pro Gly Gly Gly Ser Leu Ile Gly Arg Pro Gly
            20                  25                  30

Gly Gly Ser Val Ile Gly Arg Pro Gly Gly Ser Pro Pro Gly Gly
            35                  40                  45

Gly Ser Phe Asn Asp Glu Phe Ile Arg Asp His Ser Asp Gly Asn Arg
        50                  55                  60

Phe Ala
65

<210> SEQ ID NO 11
<211> LENGTH: 27
<212> TYPE: DNA
<213> ORGANISM: Salmo gairdneri

```
<400> SEQUENCE: 11
cgtcctgggg ttggctccat aattggt                                          27

<210> SEQ ID NO 12
<211> LENGTH: 9
<212> TYPE: PRT
<213> ORGANISM: Salmo gairdneri

<400> SEQUENCE: 12

Arg Pro Gly Val Gly Ser Ile Ile Gly
1               5

<210> SEQ ID NO 13
<211> LENGTH: 27
<212> TYPE: DNA
<213> ORGANISM: Salmo gairdneri

<400> SEQUENCE: 13
cgtcctgggg gtggctcctt aattggt                                          27

<210> SEQ ID NO 14
<211> LENGTH: 9
<212> TYPE: PRT
<213> ORGANISM: Salmo gairdneri

<400> SEQUENCE: 14

Arg Pro Gly Gly Gly Ser Leu Ile Gly
1               5

<210> SEQ ID NO 15
<211> LENGTH: 27
<212> TYPE: DNA
<213> ORGANISM: Salmo gairdneri

<400> SEQUENCE: 15
cgtcctgggg gtggctccgt aattggt                                          27

<210> SEQ ID NO 16
<211> LENGTH: 9
<212> TYPE: PRT
<213> ORGANISM: Salmo gairdneri

<400> SEQUENCE: 16

Arg Pro Gly Gly Gly Ser Val Ile Gly
1               5

<210> SEQ ID NO 17
<211> LENGTH: 27
<212> TYPE: DNA
<213> ORGANISM: Salmo gairdneri

<400> SEQUENCE: 17
cgtcctgggg gtggctctcc tcctggg                                          27

<210> SEQ ID NO 18
<211> LENGTH: 9
<212> TYPE: PRT
<213> ORGANISM: Salmo gairdneri

<400> SEQUENCE: 18

Arg Pro Gly Gly Gly Ser Pro Pro Gly
1               5
```

<210> SEQ ID NO 19
<211> LENGTH: 9
<212> TYPE: PRT
<213> ORGANISM: Salmo gairdneri
<220> FEATURE:
<221> NAME/KEY: MISC_FEATURE
<222> LOCATION: (4)..(4)
<223> OTHER INFORMATION: Xaa is Gly or Val
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ile or Pro

<400> SEQUENCE: 19

Arg Pro Gly Xaa Gly Ser Xaa Xaa Gly
1               5

<210> SEQ ID NO 20
<211> LENGTH: 856
<212> TYPE: DNA
<213> ORGANISM: Salmo gairdneri

<400> SEQUENCE: 20

```
agacatgaag atgaaggtcc aggtgagatc tctcatcctg ctcgctgtgg ctgtcctgca      60
ggtcagatct cagaaccaga ctgagaccag atatgaagac atcatctyag ttgctttgcc     120
tcagctgctt cctggggaag agcaggcttt ccgtccaatt ctgaaccagc tccaagtcga     180
gactttgaat acagaggatg tggaccagtc tgaggtgtct gtaaggctga ccttccccat     240
acaggagact ttctgtagta aatcacaggg gcagccaggc aaaccatgcc ctctgaagaa     300
aaatgggaaa ckaatgatgt gcagcatgaa rgtcagacat ccgattctgg aggcaagcaa     360
caacctgaac actgacctgt ctacatttgt ttgtgaatac atggacgcag aagatgcttt     420
gcagcagaag attcggacaa gaagaagcaa agtcagaata tgctccagag rcaaaaattg     480
tgtctctcgt cctggggttg gctccataat tggtcgtcct gggggtggct ccttaattgg     540
tcgtcctggg ggtggctccg taattggtcg tcctgggggt ggctctcctc ctggggtgg     600 ctctttcaat gatgaattta tcagagatca cagtgatgga aatcgctttg catagatcag     660
cacgctacaa cctagcacgc tacaacctct ggataactgc aaagaaccca tctatcaaag     720
aaatgtcata aggttattga tcttttttttt tgtatcaact cttacatgcc aattgttgca     780
tattatgaaa atgacttcta gattatgttt acgccaataa actgcaaaat aagtttacaa     840
aaaaaaaaaa aaaaaa                                                     856
```

<210> SEQ ID NO 21
<211> LENGTH: 216
<212> TYPE: PRT
<213> ORGANISM: Salmo gairdneri
<220> FEATURE:
<221> NAME/KEY: MISC_FEATURE
<222> LOCATION: (35)..(35)
<223> OTHER INFORMATION: Xaa is Leu or Ser
<220> FEATURE:
<221> NAME/KEY: MISC_FEATURE
<222> LOCATION: (103)..(103)
<223> OTHER INFORMATION: Xaa is Leu or Arg
<220> FEATURE:
<221> NAME/KEY: MISC_FEATURE
<222> LOCATION: (156)..(156)
<223> OTHER INFORMATION: Xaa is Gly or Asp

<400> SEQUENCE: 21

Met Lys Met Lys Val Gln Val Arg Ser Leu Ile Leu Leu Ala Val Ala
1               5                   10                  15

Val Leu Gln Val Arg Ser Gln Asn Gln Thr Glu Thr Arg Tyr Glu Asp
            20                  25                  30

Ile Ile Xaa Val Ala Leu Pro Gln Leu Leu Pro Gly Glu Glu Gln Ala
        35                  40                  45

Phe Arg Pro Ile Leu Asn Gln Leu Gln Val Glu Thr Leu Asn Thr Glu
    50                  55                  60

Asp Val Asp Gln Ser Glu Val Ser Val Arg Leu Thr Phe Pro Ile Gln
65                  70                  75                  80

Glu Thr Phe Cys Ser Lys Ser Gln Gly Gln Pro Gly Lys Pro Cys Pro
                85                  90                  95

Leu Lys Lys Asn Gly Lys Xaa Met Met Cys Ser Met Lys Val Arg His
            100                 105                 110

Pro Ile Leu Glu Ala Ser Asn Asn Leu Asn Thr Asp Leu Ser Thr Phe
        115                 120                 125

Val Cys Glu Tyr Met Asp Ala Glu Asp Ala Leu Gln Gln Lys Ile Arg
    130                 135                 140

Thr Arg Arg Ser Lys Val Arg Ile Cys Ser Arg Xaa Lys Asn Cys Val
145                 150                 155                 160

Ser Arg Pro Gly Val Gly Ser Ile Ile Gly Arg Pro Gly Gly Ser
                165                 170                 175

Leu Ile Gly Arg Pro Gly Gly Ser Val Ile Gly Arg Pro Gly Gly
            180                 185                 190

Gly Ser Pro Pro Gly Gly Gly Ser Phe Asn Asp Glu Phe Ile Arg Asp
        195                 200                 205

His Ser Asp Gly Asn Arg Phe Ala
    210                 215

<210> SEQ ID NO 22
<211> LENGTH: 451
<212> TYPE: DNA
<213> ORGANISM: Salmo gairdneri

<400> SEQUENCE: 22
atgaagatga aggtccaggt gagatctctc atcctgctcg ctgtggctgt cctgcaggtc      60
agatctcaga accagactga gaccagatat gaagacatca tctyagttgc tttgcctcag     120
ctgcttcctg gggaagagca ggctttccgt ccaattctga accagctcca agtcgagact     180
ttgaatacag aggatgtgga ccagtctgag gtgtctgtaa ggctgacctt ccccatacag     240
gagactttct gtagtaaatc acaggggcag ccaggcaaac catgccctct gaagaaaaat     300
gggaaackaa tgatgtgcag catgaargtc agacatccga ttctggaggc aagcaacaac     360
ctgaacactg acctgtctac atttgtttgt gaatacatgg acgcagaaga tgctttgcag     420
cagaagattc ggacaagaag aagcaaagtc a                                   451

<210> SEQ ID NO 23
<211> LENGTH: 150
<212> TYPE: PRT
<213> ORGANISM: Salmo gairdneri
<220> FEATURE:
<221> NAME/KEY: MISC_FEATURE
<222> LOCATION: (35)..(35)
<223> OTHER INFORMATION: Xaa is Leu or Ser
<220> FEATURE:
<221> NAME/KEY: MISC_FEATURE
<222> LOCATION: (103)..(103)
<223> OTHER INFORMATION: Xaa is Leu or Arg

<400> SEQUENCE: 23

```
Met Lys Met Lys Val Gln Val Arg Ser Leu Ile Leu Leu Ala Val Ala
1               5                   10                  15

Val Leu Gln Val Arg Ser Gln Asn Gln Thr Glu Thr Arg Tyr Glu Asp
            20                  25                  30

Ile Ile Xaa Val Ala Leu Pro Gln Leu Leu Pro Gly Glu Glu Gln Ala
        35                  40                  45

Phe Arg Pro Ile Leu Asn Gln Leu Gln Val Glu Thr Leu Asn Thr Glu
    50                  55                  60

Asp Val Asp Gln Ser Glu Val Ser Val Arg Leu Thr Phe Pro Ile Gln
65              70                  75                  80

Glu Thr Phe Cys Ser Lys Ser Gln Gly Gln Pro Gly Lys Pro Cys Pro
                85                  90                  95

Leu Lys Lys Asn Gly Lys Xaa Met Met Cys Ser Met Lys Val Arg His
            100                 105                 110

Pro Ile Leu Glu Ala Ser Asn Asn Leu Asn Thr Asp Leu Ser Thr Phe
        115                 120                 125

Val Cys Glu Tyr Met Asp Ala Glu Asp Ala Leu Gln Gln Lys Ile Arg
    130                 135                 140

Thr Arg Arg Ser Lys Val
145                 150
```

<210> SEQ ID NO 24
<211> LENGTH: 51
<212> TYPE: DNA
<213> ORGANISM: Salmo gairdneri

<400> SEQUENCE: 24
tatgaagaca tcatctcagt tgctttgcct cagctgcttc ctggggaaga g    51

<210> SEQ ID NO 25
<211> LENGTH: 17
<212> TYPE: PRT
<213> ORGANISM: Salmo gairdneri

<400> SEQUENCE: 25

```
Tyr Glu Asp Ile Ile Ser Val Ala Leu Pro Gln Leu Leu Pro Gly Glu
1               5                   10                  15

Glu
```

<210> SEQ ID NO 26
<211> LENGTH: 198
<212> TYPE: DNA
<213> ORGANISM: Salmo gairdneri

<400> SEQUENCE: 26
agaatatgct ccagagrcaa aaattgtgtc tctcgtcctg gggttggctc cataattggt    60
cgtcctgggg gtggctcctt aattggtcgt cctgggggtg gctccgtaat tggtcgtcct    120
gggggtggct ctcctcctgg ggtggctct ttcaatgatg aatttatcag agatcacagt    180
gatggaaatc gctttgca    198

<210> SEQ ID NO 27
<211> LENGTH: 66
<212> TYPE: PRT
<213> ORGANISM: Salmo gairdneri
<220> FEATURE:
<221> NAME/KEY: MISC_FEATURE
<222> LOCATION: (6)..(6)
<223> OTHER INFORMATION: Xaa is Gly or Asp

<400> SEQUENCE: 27

Arg Ile Cys Ser Arg Xaa Lys Asn Cys Val Ser Arg Pro Gly Val Gly
1               5                   10                  15

Ser Ile Ile Gly Arg Pro Gly Gly Ser Leu Ile Gly Arg Pro Gly
            20                  25                  30

Gly Gly Ser Val Ile Gly Arg Pro Gly Gly Gly Ser Pro Pro Gly Gly
        35                  40                  45

Gly Ser Phe Asn Asp Glu Phe Ile Arg Asp His Ser Asp Gly Asn Arg
    50                  55                  60

Phe Ala
65

<210> SEQ ID NO 28
<211> LENGTH: 1813
<212> TYPE: DNA
<213> ORGANISM: Salmo gairdneri

<400> SEQUENCE: 28

```
aaaataagta tatatcgaat ttagcaataa agttctattt ggtttcatc tgaccatatg      60
acattctctc aatcttcttc tggatcatcc aaatgctctc tagcaaactt cagacgggta    120
ggccaatgct atgattgatc tattgagcag accaattagg ctttgttgaa acatgtagga    180
acatttcagg aaacagatta ggccaagttc tgtataaacc atgacgacac ttcaggcggg    240
ggttccctag aagcctggat tgctcaaccc tggatttcat tgtaagaaca aaagacagac    300
tataaaacag cagaagtagg aagtaggaat cagacatgaa gatgaaggtc caggtgagat    360
ctctcatcct gctcgctgtg gctgtcctgc aggtcgatc tcagaaccag actgagacca    420
gatatgaaga catcatctya gttgcttttgc ctcagctgct tcctggggaa gagcaggctt    480
tccgtccaat tctgaaccag ctccaagtcg agactgtgag tattctgaca gtatgaatgt    540
gtccttcctt caaaaaaagt ttgtgtcatg ttttatttaa tattattctt tcagtcaagt    600
caagggataa ttgtctgttt aatatgcacc atcgtgtaca cattttccaa gtcctttatt    660
gtggaaaaga aacagactca atgtggggga atgacaattg aaatgaatga caatactata    720
agtcgcagta ttgtctttgt ctctcggaaa tcagttgaat acagaggatg tggaccagtc    780
tgaggtgtct gtaaggctga ccttccccat acaggagact ttctgtagta aatcacaggg    840
gcagccaggc aaaccatgcc ctctgaagaa aaatggggta agaacaattg gatttttacag    900
tattgtgggg gaataataat catgggaagc aggaaatgac aaataatatg ctgaggttag    960
caaatggcta attgtcaatt actccttcct ctagaaacka atgatgtgca gcatgaargt   1020
cagacatccg attctggagg caagcaacaa cctgaacact gacctgtcta catttgtttg   1080
tgaatacatg gacgcagaag atgctttgca ggtactgagc aatgcaagta tttgtcaaca   1140
ccccccttacc gacattagtt aggatgtcat gataatggta gcctaacagt gtcagatcag   1200
ttggtctgca atctaaaaat gtagatgtgg aaagtgcatt atctgcttat gaatttaatg   1260
gagattgaac ttcatgttcc ttgagatagt aaacatgcac cttatttttc tgattatact   1320
tgtctaatta ttccgatttt tcacgcaaaa aaaatgcaat gaatattttt catgattgca   1380
gcagaagatt cggacaagaa gaagcaaagt cagaatatgc tccagagrca aaaattgtgt   1440
ctctcgtcct ggggttggct ccataattgg tcgtcctggg ggtggctcct taattggtcg   1500
```

```
tcctgggggt ggctccgtaa ttggtcgtcc tggggtggc tctcctcctg ggggtggctc    1560
tttcaatgat gaatttatca gagatcacag tgatggaaat cgctttgcat agatcagcac    1620
gctacaacct agcacgctac aacctctgga taactgcaaa gaaccatct atcaaagaaa     1680 tgtcataagg ttattgatct ttttttttgt atcaactctt acatgccaat tgttgcatat    1740
tatgaaaatg acttctagat tatgtttacg ccaataaact gcaaataag tttacaaaaa    1800 aaaaaaaaaa aaa                                                       1813
```

<210> SEQ ID NO 29
<211> LENGTH: 216
<212> TYPE: PRT
<213> ORGANISM: Salmo gairdneri
<220> FEATURE:
<221> NAME/KEY: MISC_FEATURE
<222> LOCATION: (35)..(35)
<223> OTHER INFORMATION: Xaa is Leu or Ser
<220> FEATURE:
<221> NAME/KEY: MISC_FEATURE
<222> LOCATION: (103)..(103)
<223> OTHER INFORMATION: Xaa is Leu or Arg
<220> FEATURE:
<221> NAME/KEY: MISC_FEATURE
<222> LOCATION: (156)..(156)
<223> OTHER INFORMATION: Xaa is Gly or Asp

<400> SEQUENCE: 29

```
Met Lys Met Lys Val Gln Val Arg Ser Leu Ile Leu Leu Ala Val Ala
1               5                   10                  15

Val Leu Gln Val Arg Ser Gln Asn Gln Thr Glu Thr Arg Tyr Glu Asp
            20                  25                  30

Ile Ile Xaa Val Ala Leu Pro Gln Leu Pro Gly Glu Glu Gln Ala
        35                  40                  45

Phe Arg Pro Ile Leu Asn Gln Leu Gln Val Glu Thr Leu Asn Thr Glu
    50                  55                  60

Asp Val Asp Gln Ser Glu Val Ser Val Arg Leu Thr Phe Pro Ile Gln
65                  70                  75                  80

Glu Thr Phe Cys Ser Lys Ser Gln Gly Gln Pro Gly Lys Pro Cys Pro
                85                  90                  95

Leu Lys Lys Asn Gly Lys Xaa Met Met Cys Ser Met Lys Val Arg His
            100                 105                 110

Pro Ile Leu Glu Ala Ser Asn Asn Leu Asn Thr Asp Leu Ser Thr Phe
        115                 120                 125

Val Cys Glu Tyr Met Asp Ala Glu Asp Ala Leu Gln Gln Lys Ile Arg
    130                 135                 140

Thr Arg Arg Ser Lys Val Arg Ile Cys Ser Arg Xaa Lys Asn Cys Val
145                 150                 155                 160

Ser Arg Pro Gly Val Gly Ser Ile Ile Gly Arg Pro Gly Gly Ser
                165                 170                 175

Leu Ile Gly Arg Pro Gly Gly Ser Val Ile Gly Arg Pro Gly Gly
            180                 185                 190

Gly Ser Pro Pro Gly Gly Gly Ser Phe Asn Asp Glu Phe Ile Arg Asp
        195                 200                 205

His Ser Asp Gly Asn Arg Phe Ala
    210                 215
```

<210> SEQ ID NO 30
<211> LENGTH: 10
<212> TYPE: PRT

<213> ORGANISM: Sus scrofa

<400> SEQUENCE: 30

Phe Pro Pro Pro Asn Phe Pro Gly Pro Arg
1               5                   10

<210> SEQ ID NO 31
<211> LENGTH: 14
<212> TYPE: PRT
<213> ORGANISM: Sus scrofa

<400> SEQUENCE: 31

Tyr Arg Glu Ala Val Leu Arg Ala Val Asp Arg Leu Asn Glu
1               5                   10

<210> SEQ ID NO 32
<211> LENGTH: 14
<212> TYPE: PRT
<213> ORGANISM: Sus scrofa

<400> SEQUENCE: 32

Tyr Lys Glu Ala Val Leu Arg Ala Val Asp Arg Leu Asn Glu
1               5                   10

<210> SEQ ID NO 33
<211> LENGTH: 14
<212> TYPE: PRT
<213> ORGANISM: Homo sapiens

<400> SEQUENCE: 33

Tyr Lys Glu Ala Val Leu Arg Ala Ile Asp Gly Ile Asn Gln
1               5                   10

<210> SEQ ID NO 34
<211> LENGTH: 14
<212> TYPE: PRT
<213> ORGANISM: Bos taurus

<400> SEQUENCE: 34

Tyr Arg Glu Ala Val Leu Arg Ala Val Asp Gln Leu Asn Glu
1               5                   10

<210> SEQ ID NO 35
<211> LENGTH: 14
<212> TYPE: PRT
<213> ORGANISM: Ovis aries

<400> SEQUENCE: 35

Tyr Arg Glu Ala Val Leu Arg Ala Ala Asp Gln Leu Asn Glu
1               5                   10

<210> SEQ ID NO 36
<211> LENGTH: 14
<212> TYPE: PRT
<213> ORGANISM: Ovis aries

<400> SEQUENCE: 36

Tyr Arg Glu Ala Val Leu Arg Ala Val Gly Gln Leu Asn Glu
1               5                   10

<210> SEQ ID NO 37
<211> LENGTH: 14
<212> TYPE: PRT
<213> ORGANISM: Bos taurus

```
<400> SEQUENCE: 37

Tyr Arg Glu Ala Val Leu Arg Ala Val Asp Gln Phe Asn Glu
1               5                   10

<210> SEQ ID NO 38
<211> LENGTH: 14
<212> TYPE: PRT
<213> ORGANISM: Mus sp.

<400> SEQUENCE: 38

Tyr Arg Asp Ala Val Leu Arg Ala Val Asp Asp Phe Asn Gln
1               5                   10

<210> SEQ ID NO 39
<211> LENGTH: 14
<212> TYPE: PRT
<213> ORGANISM: Homo sapiens

<400> SEQUENCE: 39

Tyr Arg Glu Ala Val Leu Arg Ala Val Asp Ala Phe Asn Gln
1               5                   10

<210> SEQ ID NO 40
<211> LENGTH: 14
<212> TYPE: PRT
<213> ORGANISM: Mus sp.

<400> SEQUENCE: 40

Tyr Glu Glu Ile Val Asp Arg Ala Ile Glu Ala Tyr Asn Gln
1               5                   10

<210> SEQ ID NO 41
<211> LENGTH: 14
<212> TYPE: PRT
<213> ORGANISM: Oryctolagus cuniculus

<400> SEQUENCE: 41

Tyr Glu Glu Val Val Ala Gln Ala Leu Gln Phe Tyr Asn Glu
1               5                   10

<210> SEQ ID NO 42
<211> LENGTH: 17
<212> TYPE: PRT
<213> ORGANISM: Salmo gairdneri

<400> SEQUENCE: 42

Tyr Glu Asp Ile Ile Leu Val Ala Leu Pro Gln Leu Leu Pro Gly Glu
1               5                   10                  15

Glu

<210> SEQ ID NO 43
<211> LENGTH: 23
<212> TYPE: PRT
<213> ORGANISM: Sus scrofa

<400> SEQUENCE: 43

Phe Thr Val Lys Glu Thr Val Cys Pro Arg Pro Thr Arg Gln Pro Pro
1               5                   10                  15

Glu Leu Cys Asp Phe Lys Glu
                20

<210> SEQ ID NO 44
<211> LENGTH: 23
```

```
<212> TYPE: PRT
<213> ORGANISM: Homo sapiens

<400> SEQUENCE: 44

Phe Thr Val Lys Glu Thr Val Cys Pro Arg Thr Thr Gln Gln Ser Pro
1               5                   10                  15

Glu Asp Cys Asp Phe Lys Lys
            20

<210> SEQ ID NO 45
<211> LENGTH: 23
<212> TYPE: PRT
<213> ORGANISM: Sus scrofa

<400> SEQUENCE: 45

Phe Thr Val Lys Glu Thr Val Cys Pro Arg Pro Thr Arg Arg Pro Pro
1               5                   10                  15

Glu Leu Cys Asp Phe Lys Glu
            20

<210> SEQ ID NO 46
<211> LENGTH: 23
<212> TYPE: PRT
<213> ORGANISM: Sus scrofa

<400> SEQUENCE: 46

Phe Thr Val Lys Glu Thr Val Cys Pro Arg Pro Thr Trp Arg Pro Pro
1               5                   10                  15

Glu Leu Cys Asp Phe Lys Glu
            20

<210> SEQ ID NO 47
<211> LENGTH: 23
<212> TYPE: PRT
<213> ORGANISM: Bos taurus

<400> SEQUENCE: 47

Phe Arg Val Lys Glu Thr Val Cys Ser Arg Thr Thr Gln Gln Pro Pro
1               5                   10                  15

Glu Gln Cys Asp Phe Lys Glu
            20

<210> SEQ ID NO 48
<211> LENGTH: 23
<212> TYPE: PRT
<213> ORGANISM: Ovis aries

<400> SEQUENCE: 48

Phe Arg Val Lys Glu Thr Val Cys Pro Arg Thr Ser Gln Gln Pro Ala
1               5                   10                  15

Glu Gln Cys Asp Phe Lys Glu
            20

<210> SEQ ID NO 49
<211> LENGTH: 23
<212> TYPE: PRT
<213> ORGANISM: Ovis aries

<400> SEQUENCE: 49

Phe Arg Val Lys Glu Thr Val Cys Pro Arg Met Ser Gln Gln Pro Pro
1               5                   10                  15

Glu Gln Cys Asp Phe Lys Glu
```

```
          20

<210> SEQ ID NO 50
<211> LENGTH: 23
<212> TYPE: PRT
<213> ORGANISM: Ovis aries

<400> SEQUENCE: 50

Phe Arg Val Lys Glu Thr Val Cys Pro Arg Met Thr Gln Gln Pro Pro
1               5                   10                  15

Glu Gln Cys Asp Phe Lys Glu
            20

<210> SEQ ID NO 51
<211> LENGTH: 23
<212> TYPE: PRT
<213> ORGANISM: Bos taurus

<400> SEQUENCE: 51

Phe Arg Val Lys Glu Thr Val Cys Pro Arg Thr Ser Gln Gln Pro Leu
1               5                   10                  15

Glu Gln Cys Asp Phe Lys Glu
            20

<210> SEQ ID NO 52
<211> LENGTH: 23
<212> TYPE: PRT
<213> ORGANISM: Bos taurus

<400> SEQUENCE: 52

Phe Thr Val Lys Glu Thr Val Cys Pro Arg Thr Ile Gln Gln Pro Ala
1               5                   10                  15

Glu Gln Cys Asp Phe Lys Glu
            20

<210> SEQ ID NO 53
<211> LENGTH: 23
<212> TYPE: PRT
<213> ORGANISM: Equus sp.

<400> SEQUENCE: 53

Phe Met Val Lys Glu Thr Val Cys Pro Arg Ile Met Lys Gln Thr Pro
1               5                   10                  15

Glu Gln Cys Asp Phe Lys Glu
            20

<210> SEQ ID NO 54
<211> LENGTH: 23
<212> TYPE: PRT
<213> ORGANISM: Mus sp.

<400> SEQUENCE: 54

Phe Arg Val Lys Glu Thr Val Cys Gly Lys Ala Glu Arg Gln Leu Pro
1               5                   10                  15

Glu Gln Cys Ala Phe Lys Glu
            20

<210> SEQ ID NO 55
<211> LENGTH: 23
<212> TYPE: PRT
<213> ORGANISM: Homo sapiens

<400> SEQUENCE: 55
```

```
Phe Thr Val Lys Glu Thr Glu Cys Pro Arg Thr Thr Trp Lys Leu Pro
1               5                   10                  15

Glu Gln Cys Asp Phe Lys Glu
            20

<210> SEQ ID NO 56
<211> LENGTH: 23
<212> TYPE: PRT
<213> ORGANISM: Mus sp.

<400> SEQUENCE: 56

Phe Arg Ile Lys Glu Thr Glu Cys Thr Ser Thr Gln Glu Arg Gln Pro
1               5                   10                  15

Lys Asp Cys Asp Phe Leu Glu
            20

<210> SEQ ID NO 57
<211> LENGTH: 23
<212> TYPE: PRT
<213> ORGANISM: Oryctolagus cuniculus

<400> SEQUENCE: 57

Phe Arg Ile Lys Glu Thr Val Cys Ile Phe Thr Leu Asp Arg Gln Pro
1               5                   10                  15

Gly Asn Cys Ala Phe Arg Glu
            20

<210> SEQ ID NO 58
<211> LENGTH: 23
<212> TYPE: PRT
<213> ORGANISM: Salmo gairdneri

<400> SEQUENCE: 58

Phe Pro Ile Gln Glu Thr Phe Cys Ser Lys Ser Gln Gly Gln Pro Gly
1               5                   10                  15

Lys Pro Cys Pro Leu Lys Lys
            20

<210> SEQ ID NO 59
<211> LENGTH: 43
<212> TYPE: PRT
<213> ORGANISM: Sus scrofa

<400> SEQUENCE: 59

Val Arg Arg Arg Pro Arg Pro Pro Tyr Leu Pro Arg Pro Arg Pro Pro
1               5                   10                  15

Pro Phe Phe Pro Pro Arg Leu Pro Pro Arg Ile Pro Pro Gly Phe Pro
            20                  25                  30

Pro Arg Phe Pro Pro Arg Phe Pro Gly Lys Arg
        35                  40

<210> SEQ ID NO 60
<211> LENGTH: 39
<212> TYPE: PRT
<213> ORGANISM: Homo sapiens

<400> SEQUENCE: 60

Ala Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30
```

```
Val Pro Arg Thr Glu Ser Asp
        35

<210> SEQ ID NO 61
<211> LENGTH: 20
<212> TYPE: PRT
<213> ORGANISM: Sus scrofa

<400> SEQUENCE: 61

Val Arg Gly Gly Arg Leu Cys Tyr Cys Arg Arg Phe Cys Val Cys
1               5                   10                  15

Val Gly Arg Gly
        20

<210> SEQ ID NO 62
<211> LENGTH: 24
<212> TYPE: PRT
<213> ORGANISM: Sus scrofa

<400> SEQUENCE: 62

Val Arg Ile Ile Asp Leu Leu Trp Arg Val Arg Arg Pro Gln Lys Pro
1               5                   10                  15

Lys Phe Val Thr Val Trp Val Arg
        20

<210> SEQ ID NO 63
<211> LENGTH: 37
<212> TYPE: PRT
<213> ORGANISM: Sus scrofa

<400> SEQUENCE: 63

Val Gly Arg Phe Arg Arg Leu Arg Lys Lys Thr Arg Lys Arg Leu Lys
1               5                   10                  15

Lys Ile Gly Lys Val Leu Lys Trp Ile Pro Pro Ile Val Gly Ser Ile
            20                  25                  30

Pro Leu Gly Cys Gly
        35

<210> SEQ ID NO 64
<211> LENGTH: 13
<212> TYPE: PRT
<213> ORGANISM: Bos taurus

<400> SEQUENCE: 64

Ala Arg Leu Cys Arg Ile Val Val Ile Arg Val Cys Arg
1               5                   10

<210> SEQ ID NO 65
<211> LENGTH: 31
<212> TYPE: PRT
<213> ORGANISM: Ovis aries

<400> SEQUENCE: 65

Val Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Leu
            20                  25                  30

<210> SEQ ID NO 66
<211> LENGTH: 61
<212> TYPE: PRT
<213> ORGANISM: Ovis aries
```

-continued

```
<400> SEQUENCE: 66

Val Arg Arg Leu Arg Pro Arg Pro Arg Leu Pro Arg Pro Arg Pro
1               5                   10                  15

Arg Pro Arg Pro Arg Pro Ser Leu Pro Leu Pro Arg Pro Gln Pro
                20                  25                  30

Arg Arg Ile Pro Arg Pro Ile Leu Leu Pro Trp Arg Pro Arg Pro
            35                  40                  45

Ile Pro Arg Pro Gln Pro Gln Pro Ile Pro Arg Trp Leu
        50                  55                  60

<210> SEQ ID NO 67
<211> LENGTH: 53
<212> TYPE: PRT
<213> ORGANISM: Ovis aries

<400> SEQUENCE: 67

Val Arg Arg Leu Arg Pro Arg His Gln His Phe Pro Ser Glu Arg Pro
1               5                   10                  15

Trp Pro Lys Pro Leu Pro Leu Pro Leu Pro Arg Pro Gly Pro Arg Pro
                20                  25                  30

Trp Pro Lys Pro Leu Pro Leu Pro Leu Pro Arg Pro Gly Leu Arg Pro
            35                  40                  45

Trp Pro Lys Pro Leu
        50

<210> SEQ ID NO 68
<211> LENGTH: 48
<212> TYPE: PRT
<213> ORGANISM: Bos taurus

<400> SEQUENCE: 68

Val Arg Phe Arg Pro Pro Ile Arg Arg Pro Pro Ile Arg Pro Pro Phe
1               5                   10                  15

Tyr Pro Pro Phe Arg Pro Pro Ile Arg Pro Pro Ile Phe Pro Pro Ile
                20                  25                  30

Arg Pro Pro Phe Arg Pro Pro Leu Gly Pro Phe Pro Gly Arg Arg Leu
            35                  40                  45

<210> SEQ ID NO 69
<211> LENGTH: 67
<212> TYPE: PRT
<213> ORGANISM: Salmo gairdneri

<400> SEQUENCE: 69

Val Arg Ile Cys Ser Arg Asp Lys Asn Cys Val Ser Arg Pro Gly Val
1               5                   10                  15

Gly Ser Ile Ile Gly Arg Pro Gly Gly Ser Leu Ile Gly Arg Pro
                20                  25                  30

Gly Gly Gly Ser Val Ile Gly Arg Pro Gly Gly Gly Ser Pro Pro Gly
            35                  40                  45

Gly Gly Ser Phe Asn Asp Glu Phe Ile Arg Asp His Ser Asp Gly Asn
        50                  55                  60

Arg Phe Ala
65

<210> SEQ ID NO 70
<211> LENGTH: 22
<212> TYPE: DNA
```

```
<213> ORGANISM: artificial sequence
<220> FEATURE:
<223> OTHER INFORMATION: Primer

<400> SEQUENCE: 70
atcgtggggc gccccaggca cc                                                   22

<210> SEQ ID NO 71
<211> LENGTH: 24
<212> TYPE: DNA
<213> ORGANISM: artificial sequence
<220> FEATURE:
<223> OTHER INFORMATION: Primer

<400> SEQUENCE: 71
ctccttaatg tcacgcacga tttc                                                 24

<210> SEQ ID NO 72
<211> LENGTH: 21
<212> TYPE: DNA
<213> ORGANISM: artificial sequence
<220> FEATURE:
<223> OTHER INFORMATION: Primer

<400> SEQUENCE: 72
ggattcacaa gaactaagga c                                                    21

<210> SEQ ID NO 73
<211> LENGTH: 20
<212> TYPE: DNA
<213> ORGANISM: artificial sequence
<220> FEATURE:
<223> OTHER INFORMATION: Primer

<400> SEQUENCE: 73
cttagttgtg gcgctggatg                                                      20

<210> SEQ ID NO 74
<211> LENGTH: 25
<212> TYPE: DNA
<213> ORGANISM: artificial sequence
<220> FEATURE:
<223> OTHER INFORMATION: Primer

<400> SEQUENCE: 74
actacaaaac agccaactac aaacc                                                25

<210> SEQ ID NO 75
<211> LENGTH: 19
<212> TYPE: DNA
<213> ORGANISM: artificial sequence
<220> FEATURE:
<223> OTHER INFORMATION: Primer

<400> SEQUENCE: 75
ctctgctgct ggcttcagt                                                       19

<210> SEQ ID NO 76
<211> LENGTH: 15
<212> TYPE: DNA
<213> ORGANISM: artificial sequence
<220> FEATURE:
<223> OTHER INFORMATION: Primer

<400> SEQUENCE: 76
tctgagaaca agtgc                                                           15
```

<210> SEQ ID NO 77
<211> LENGTH: 21
<212> TYPE: DNA
<213> ORGANISM: artificial sequence
<220> FEATURE:
<223> OTHER INFORMATION: Primer

<400> SEQUENCE: 77
cgaattcatg gatttgagtc a                                            21

<210> SEQ ID NO 78
<211> LENGTH: 20
<212> TYPE: DNA
<213> ORGANISM: artificial sequence
<220> FEATURE:
<223> OTHER INFORMATION: Primer

<400> SEQUENCE: 78
aattaaccct cactaaaggg                                              20

<210> SEQ ID NO 79
<211> LENGTH: 22
<212> TYPE: DNA
<213> ORGANISM: artificial sequence
<220> FEATURE:
<223> OTHER INFORMATION: Primer

<400> SEQUENCE: 79
cattatgctg agtgatatcc cg                                           22

<210> SEQ ID NO 80
<211> LENGTH: 23
<212> TYPE: DNA
<213> ORGANISM: artificial sequence
<220> FEATURE:
<223> OTHER INFORMATION: Primer

<400> SEQUENCE: 80
catcctgctc gctgtggctg tcc                                          23

<210> SEQ ID NO 81
<211> LENGTH: 23
<212> TYPE: DNA
<213> ORGANISM: artificial sequence
<220> FEATURE:
<223> OTHER INFORMATION: Primer

<400> SEQUENCE: 81
cctccagaat cggatgtctg acc                                          23

<210> SEQ ID NO 82
<211> LENGTH: 18
<212> TYPE: DNA
<213> ORGANISM: artificial sequence
<220> FEATURE:
<223> OTHER INFORMATION: Primer

<400> SEQUENCE: 82
atggaagatg aaatcgcc                                                18

<210> SEQ ID NO 83
<211> LENGTH: 18
<212> TYPE: DNA
<213> ORGANISM: artificial sequence
<220> FEATURE:

```
<223> OTHER INFORMATION: Primer

<400> SEQUENCE: 83
tgccagatct tctccatg                                                  18

<210> SEQ ID NO 84
<211> LENGTH: 27
<212> TYPE: DNA
<213> ORGANISM: artificial sequence
<220> FEATURE:
<223> OTHER INFORMATION: Primer

<400> SEQUENCE: 84
acaatttttg cctctggagc atattct                                        27

<210> SEQ ID NO 85
<211> LENGTH: 28
<212> TYPE: DNA
<213> ORGANISM: artificial sequence
<220> FEATURE:
<223> OTHER INFORMATION: Primer

<400> SEQUENCE: 85
cacaaacaaa tgtagacagg tcagtgtt                                       28
```

PEPTIDES AND NUCLEIC ACIDS OF THE CATHELICIDIN FAMILY, DERIVED FROM FISH, AND USES THEREOF

This application is a §371 application of PCT/GB03/00322 filed 27 Jan. 2003, which in turn claims priority to GB applications 0201744.0 filed 25 Jan. 2002, and 0214660.3 filed 25 Jun. 2002. Each of the above identified applications is incorporated by reference herein.

The present invention relates to molecules having anti-microbial and immunostimulatory activity, and in particular to anti-microbial and immunostimulatory peptides of the cathelicidin family.

Vertebrates have evolved a wide range of mechanisms to counter infection by microbes. These include generation of inorganic microbicidal molecules, such as active oxygen species, by specialist phagocytic cells, as well as more sophisticated enzyme- or cell-mediated defensive systems.

Mammals are known to produce a range of anti-microbial peptides which primarily exert their effects via interaction with the microbial cell membrane. One of these families is the cathelicidin family.

Cathelicidins are synthesised as prepropeptides in myeloid cells, processed by the removal of the signal peptide and stored as propeptides in the cytoplasmic granules of neutrophil leukocytes. The propeptide contains the well conserved cathelin domain, characteristic of the family, and is not of itself microbicidal. The reason for the high degree of conservation is unclear, but the prosequence may have a role in targeting the propeptide to the granules or ensuring appropriate proteolytic maturation.

The antimicrobial activity resides in the mature peptide, which is released on cleavage from the propeptide by elastase. Elastase cleavage occurs C-terminal of valine residues predominantly, and occasionally after alanine residues.

The cathelicidin family is divided into five different groups according to the structure of the anti-microbial mature peptide, the sequences of which are highly variable. The family includes peptides with two disulfide bonds (protegrins), peptides with one disulfide bond (cyclic dodecapeptide), peptides rich in proline and arginine residues with short modules arranged in tandem repeats (bactenecins, PR-39, prophenins), peptides rich in tryptophan residues (indolicidin, PMAP-23), and peptides with α-helical structure (PMAP-36 and -37, CAP18, FALL-39) (Zanetti et al., 1995).

Bovine bactenecins include three tandem repeats of a tetradecamer characterised by several Pro-Arg-Pro triplets spaced by single hydrophobic amino acids (Frank et al., 1990). Pig prophenins contain three perfect repeats of a decamer FPPPNFPGPR (SEQ ID NO: 30) (Harwig et al., 1995).

The mechanism of action of these peptides varies from rapidly permeating the bacterial membrane to inhibition of macromolecular synthesis in gram-negative bacteria. In addition to the microbial activity, some peptides are able to neutralise the effects of LPS, induce wound repair and inhibit tissue degradation as part of the protection of the host.

An analogue of protegrin-1 is in clinical trials for the treatment of polymicrobial oral mucositis (Chen et al. Biopolymers (Peptide Science) 55: 88-98 (2000)).

The present inventors have now cloned a cDNA from rainbow trout which contains an open reading frame believed to encode the first example of a non-mammalian cathelicidin. This was unexpectedly achieved while investigating the presence of IL-1β-related genes in rainbow trout.

As described above, cathelicidins are typically synthesised in vivo as prepropeptides, having a signal peptide, a propeptide portion and a mature peptide portion. The particular cathelicidin described in the Examples conforms to this general structure as shown in FIG. 10; cDNA sequences and predicted amino acid sequence are shown in FIG. 8 and by SEQ ID NOs: 1 and 2, and 20 and 21.

Although the cDNA clone obtained was incomplete, the first 20 amino acids of the predicted polypeptide sequence had the characteristics of a signal peptide, suggesting that the open reading frame was largely complete, with little remaining to be cloned. The sequence of the full-length ORF shown in SEQ ID NO: 20 (from nucleotides 5 to 655) confirms this, the full length ORF encoding only two more amino acids than that shown in FIG. 8.

Sequencing of the full length ORF revealed the presence of four single nucleotide polymorphisms, three of which are predicted to result in variation of the encoded amino acid. Where a sequence shown herein includes one or more polymorphisms, all individual sequence permutations arising from those polymorphisms are considered to be disclosed and to form part of the present invention.

In this document, nucleotides or amino acid residues are numbered as in FIG. 8, SEQ ID NO:1 and SEQ ID NO: 2 except where otherwise stated.

Although the proteolytic cleavage sites have yet to be confirmed, amino acids 21 to 148 of SEQ ID NO: 2 are believed to constitute the propeptide region, and amino acids 149 to 214 the 'mature' anti-microbial peptide.

The predicted propeptide region (SEQ ID NOs: 3 and 4, 22 and 23) contains two cathelin signature sequences—residues 28 to 44 (SEQ ID NOs: 5 and 6), and 75 to 97 (SEQ ID NOs: 7 and 8). A polymorphism in the propeptide region provides an alternative sequence for the cathelin signature of residues 28 to 44, shown as SEQ ID NOs: 24 and 25. The propeptide region is further predicted to contain two internal disulphide bonds, between cysteine residues 82 and 93, and 104 and 128 of SEQ ID NO: 2. The propeptide region has no more than 29% similarity at the amino acid level with any published mammalian cathelicidin sequence.

The 66 amino acid anti-microbial peptide region (SEQ ID NO: 9 and 10, 26 and 27) has similarities with two groups of mammalian cathelicidins. It is predicted to have an internal disulphide bridge between residues 151 and 157 of SEQ ID NO:2, characteristic of the dodecapeptide group, and also contains four tandem repeats of a nonameric consensus sequence RPG-G/V-GS-X-I/P-G (SEQ ID NO: 19), similar to the repeats found in the prophenin group. As a result the present inventors have classified this polypeptide in the prophenin group, and designated it 'trout bactenecin'.

Thus in one aspect of the present invention, there is provided a non-mammalian cathelicidin polypeptide, in particular, a piscine cathelicidin.

The cathelicidin of the present invention may comprise the whole or part of the amino acid sequence of SEQ ID NO: 2 or 21. It may be encoded by a nucleic acid comprising all or part of nucleotides 1 to 647 of SEQ ID NO:1, the whole or part of SEQ ID NO: 20, or the whole or part of SEQ ID NOs: 3 or 22, or 9 or 26, or by a mutant, variant, derivative, allele, homologue, orthologue or paralogue thereof. The polypeptide sequence encoded, or a portion thereof, may show greater than about 40% homology with SEQ ID NOs: 2, 21, 4, 23, 10 or 27, greater than about 50% homology, greater than about 60% homology, greater than about 70% homology, greater than about 80% homology, greater than about 90% homology or greater than about 95% homology with any one of these sequences.

The term "homology" is used throughout this specification to refer to percentage identity as between two sequences. Percentage identity may be calculated using a program such as BLAST or BestFit from within the Genetics Computer Group (GCG) Version 10 software package available from the University of Wisconsin, using default parameters.

It will be appreciated that subregions of the cathelicidin may have independent utility. These subregions may be individual domains, subdomains, or peptides derived from e.g. the complete molecule, the propeptide region or the mature peptide.

Thus the present invention further provides an isolated peptide or polypeptide, comprising a portion having anti-microbial activity, from a non-mammalian cathelicidin, for example from a piscine cathelicidin.

Anti-microbial in this context signifies an ability to retard the growth of, or kill, one or more eukaryotic or prokaryotic microbes, e.g. a fungus such as a yeast, or a bacterium. Assays for determining anti-microbial activity may be based on those previously described, e.g. in PCT/US00/22781, U.S. Pat. No. 6,172,185, EP-A-665 239, Genarro et al. (1989), and Gennaro et al. (1998).

The portion having anti-microbial activity may comprise the amino acid sequence RPG-G/V-GS-X-I/P-G (SEQ ID NO: 19), e.g. two to four repeats of the amino acid sequence RPG-G/V-GS-X-I/P-G (SEQ ID NO: 19). One or more of these repeats may have the sequence of SEQ ID NOs: 12, 14, 16 or 18. In one embodiment, the portion having anti-microbial activity may comprise one of each of SEQ ID NOs: 12, 14, 16 and 18.

The portion having anti-microbial activity may further comprise a pair of cysteine residues capable of forming an internal disulphide bridge.

In one embodiment, the portion having anti-microbial activity comprises the amino acid sequence of SEQ ID NO: 10 or 27. Alternatively, the portion having anti-microbial activity may show greater than about 40% homology with SEQ ID NO: 10 or 27, greater than about 50% homology, greater than about 60% homology, greater than about 70% homology, greater than about 80% homology, greater than about 90% homology or greater than about 95% homology therewith.

The isolated polypeptide may further comprise a propeptide portion cleavable from the portion having anti-microbial activity by a protease. The isolated polypeptide may have anti-microbial activity in its own right. Alternatively, the portion having anti-microbial activity may be able to display anti-microbial activity only when cleaved from the propeptide portion.

In one embodiment, the protease is elastase. Proteolytic cleavage by elastase occurs C-terminal of small uncharged residues such as valine or alanine, in cathelicidins typically C-terminal of a valine residue. Consequently, the C-terminal residue of the propeptide will typically be valine.

Typically, the propeptide portion comprises one or more cathelin signature sequences; for example, the propeptide portion may comprise one or more of SEQ ID NOs: 6, 25 and 8; preferably two of SEQ ID NOs: 6, 25 and 8.

Additionally or alternatively, the propeptide portion may comprise at least one pair of cysteine residues capable of forming an internal disulphide bridge. In one embodiment, the propeptide portion comprises at least two pairs of cysteine residues capable of forming internal disulphide bridges.

In a particular embodiment, the propeptide portion may comprise the amino acid sequence of SEQ ID NO: 4 or 23.

Alternatively, the propeptide portion of the polypeptide sequence may show greater than about 40% homology with SEQ ID NO: 4 or 23, greater than about 50% homology, greater than about 60% homology, greater than about 70% homology, greater than about 80% homology, greater than about 90% homology or greater than about 95% homology therewith.

It is known that the propeptides of mammalian cathelicidins are often extensively conserved within a particular family. Although the propeptide described in the Examples has only 29% similarity at the amino acid level with known cathelicidins, it may share considerably more homology with the propeptide regions of as-yet unidentified cathelicidins, such as non-mammalian cathelicidins, e.g. piscine cathelicidins. Therefore the present invention enables the identification of novel cathelicidin polypeptides and coding sequences from non-mammalian species, e.g. piscine species.

Accordingly, the present invention further provides an isolated polypeptide, comprising a portion having anti-microbial activity, and a propeptide portion cleavable from the portion having anti-microbial activity by a protease, the propeptide portion comprising one or more of SEQ ID NOs: 6, 25 and 8, preferably two of SEQ ID NOs: 6, 25 and 8.

The propeptide portion may further comprise at least one pair of cysteine residues capable of forming an internal disulphide bridge, preferably at least two pairs of cysteine residues capable of forming internal disulphide bridges.

The propeptide portion may comprise the amino acid sequence of SEQ ID NO: 4 or 23, or may show greater than about 40% homology with SEQ ID NO: 4, greater than about 50% homology, greater than about 60% homology, greater than about 70% homology, greater than about 80% homology, greater than about 90% homology or greater than about 95% homology therewith.

The prospect that as-yet unidentified cathelicidins may be homologous to the propeptide of the trout bactenecin molecule provided herein raises the possibility that the propeptide itself may be used to identify further cathelicidins. For example, the propeptide may be used to raise antibodies which can then be used to screen expression libraries for related molecules (see below). The propeptide may be used in preliminary assays to determine particularly antigenic epitopes thereof. These epitopes may then be synthesised or expressed independently for the purposes of raising antibodies. Accordingly, the present invention also provides an isolated propeptide region from a non-mammalian cathelicidin, for example, an isolated propeptide region from a piscine cathelicidin, as well as antigenic portions thereof.

The isolated propeptide or portion thereof may comprise at least one, and preferably two of SEQ ID NOs: 6, 25 and 8. It may further comprise at least one pair of cysteine residues capable of forming an internal disulphide bridge, preferably at least two pairs of cysteine residues capable of forming internal disulphide bridges.

In particular embodiments, the isolated polypeptide may comprise the amino acid sequence of SEQ ID NO: 4 or 23, or may show greater than about 40% homology, greater than about 50% homology, greater than about 60% homology, greater than about 70% homology, greater than about 80% homology, greater than about 90% homology or greater than about 95% homology therewith.

The isolated polypeptides and peptides described herein will typically be free or substantially free of material with which they are naturally associated, such as piscine or other physiological host polypeptides other than cathelicidins. Additionally or alternatively, for example, if expressed in a prokaryotic or other recombinant host cell, they may be lacking in native glycosylation, e.g. alternatively glycosylated or unglycosylated). As a further alternative, the polypeptides or peptides of the present invention may by generated by chemical synthesis, techniques for which are well known to those of ordinary skill in the art.

The polypeptides and peptides of the present invention may be amidated at the C terminus or be in a free acid form. They may be extended at the 5' end or 3' end thereof relative to any of the peptide sequences detailed herein, e.g. SEQ ID NOs: 2, 21, 4, 23, 6 or 25. For example, the open reading frame may comprise a sequence encoding a signal peptide, such as a full length native signal peptide (e.g. an extended form of the putative truncated signal peptide coding sequence shown as amino acids 1 to 20 of SEQ ID NO: 1) such as amino acids 1 to 22 of SEQ ID NO: 21, a heterologous signal peptide, or a combination thereof, in order to ensure appropriate secretion when expressed from a recombinant host cell.

Particularly when produced by expression from a recombinant host, the peptides or polypeptides of the present invention may comprise a signal peptide. This may be a full length native signal peptide (e.g. an extended form of the putative truncated signal peptide shown as amino acids 1 to 20 of SEQ ID NO: 2) such as amino acids 1 to 22 of SEQ ID NO: 21, or a heterologous signal peptide, in order to ensure appropriate secretion from the recombinant host cell.

In a further aspect, the present invention provides nucleic acids encoding the peptides and polypeptides as described herein. Thus the present invention provides a nucleic acid encoding a non-mammalian cathelicidin. In preferred embodiments the nucleic acid encodes a piscine cathelicidin.

The nucleic acids may be wholly or partially synthetic. In particular they may be recombinant in that nucleic acid sequences which are not found together in nature (do not run contiguously) have been ligated or otherwise combined artificially. Alternatively they may have been synthesised directly e.g. using an automated synthesiser.

Nucleic acid according to the present invention may be polynucleotides or oligonucleotides, and may include cDNA, RNA, genomic DNA (gDNA) and modified nucleic acids or nucleic acid analogs. Where a DNA sequence is specified, e.g. with reference to a figure or SEQ ID NO., unless context requires otherwise the RNA equivalent, with U substituted for T where it occurs, is encompassed.

Nucleic acids may comprise, consist or consist essentially of any of the sequences disclosed herein (which may be a gene, a genomic clone or other sequence, a cDNA, or an ORF or exon of any of these etc.). For example, where gDNA is disclosed, nucleic acids comprising any one or more introns or exons from any of the gDNA are also embraced. Likewise, where cDNA is disclosed, nucleic acids comprising only the translated region (from initiation to termination codons) are also embraced.

Where a nucleic acid (or nucleotide sequence) of the invention is referred to herein, the complement of that nucleic acid (or nucleotide sequence) will also be embraced by the invention. The 'complement' in each case is the same length as the reference, but is 100% complementary thereto whereby by each nucleotide is base paired to its counterpart i.e. G to C, and A to T or U.

The nucleic acids of the present invention may differ from the specific sequences recited herein by a change which is one or more of addition, insertion, deletion and substitution of one or more nucleotides of the sequences shown, e.g. 1, 2, 3, 4, 5, 6, 7, 8, 9, 10, 15, 20, 25, 30, 40, 50 or more nucleotides. Changes to a nucleotide sequence may result in an amino acid change at the protein level, or not, as determined by the degeneracy of the genetic code.

On the other hand the encoded polypeptides may comprise an amino acid sequence which differs by one or more amino acid residues from the amino acid sequences shown herein, as discussed above. Nucleic acids encoding polypeptides which are amino acid sequence variants, derivatives, alleles, mutants, homologues, orthologues or paralogues of the sequences shown herein are further provided by the present invention. Nucleic acid encoding such a polypeptide may show greater than about 40% homology with any of the coding sequences shown herein, greater than about 50% homology, greater than about 60% homology, greater than about 70% homology, greater than about 80% homology, greater than about 90% homology or greater than about 95% homology with e.g. SEQ ID NOs. 1, 3, 5, 7, 9, 11, 13, 15, 17, 20, 22, 24 or 26.

The open reading frame of nucleic acids encoding a polypeptide or peptide according to the present invention may be extended at the 5' end or 3' end thereof relative to any of the coding sequences detailed herein, e.g. nucleotides 1 to 644 of SEQ ID NO: 1, SEQ ID NO: 3 or SEQ ID NO: 9. The open reading frame may comprise a sequence encoding a signal peptide, such as a full length native signal peptide (e.g. an extended form of the putative truncated signal peptide coding sequence shown as nucleotides 1 to 62 of SEQ ID NO: 1), a heterologous signal peptide, or a combination thereof, in order to ensure appropriate secretion when expressed from a recombinant host cell. For example the ORF may be as shown in FIG. 15 or SEQ ID NO: 20.

The term 'orthologous' is used herein to refer to a gene at an equivalent chromosomal locus to a given gene but in a different species. The term 'paralogous' refers to a gene present at a different chromosomal locus to a given gene, in the same or a different species, but homologous to that gene and related to it by a gene duplication event.

Nucleic acids of the present invention may be provided as part of a vector, and also provided by the present invention is a vector comprising nucleic acid as described herein, particularly vectors from which the polypeptide can be expressed under appropriate conditions, and a host cell containing any such vector or nucleic acid.

'Vector' is defined to include, inter alia, any plasmid, cosmid, phage or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably a nucleic acid sequence of the present invention in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus this aspect of the invention provides a gene construct, preferably a replicable vector, comprising a promoter (optionally inducible) operably linked to a nucleotide sequence provided by the present invention, such as the trout bactenecin gene or a variant thereof.

The present invention also encompasses a method of making a polypeptide or peptide as disclosed, the method including the step of expressing said polypeptide or peptide from nucleic acid encoding it, which in most embodiments will be nucleic acid according to the present invention. This may conveniently be achieved by growing a host cell containing such a vector in culture under appropriate conditions which cause or allow expression of the polypeptide. Polypeptides and peptides may also be expressed in in vitro systems, such as reticulocyte lysates, as will be appreciated by the skilled person.

Systems for cloning and expression of a polypeptide in a variety of different host cells are well known. Suitable host cells include bacteria, eukaryotic cells such as mammalian cells, fish cells and yeast, and baculovirus systems. Mammalian cell lines available in the art for expression of a heterologous polypeptide include Chinese hamster ovary cells, HeLa cells, baby hamster kidney cells, COS cells and many others. A candidate fish cell line is the trout fibroblast line RTG. A common, preferred bacterial host is *E. coli*. However, typically, a host will be chosen which is not so adversely affected by any anti-microbial effects of the expressed protein as to impair the yield of expressed protein or peptide. Thus the choice of host may depend upon the particular activity of the peptide or protein to be expressed.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as 'transformation', may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

The cloning by the present inventors of the trout bactenecin molecule further provides valuable material for use in identification and isolation of further cathelicidins, particularly from non-mammalian species, especially piscine species.

Thus in another aspect, the present invention provides an isolated nucleic acid for use as a probe or primer, said nucleic acid comprising a distinctive sequence of at least about 16 to 24 nucleotides in length, said distinctive sequence being present in nucleotides 1 to 815 of SEQ ID NO:1, or in any of SEQ ID NO: 20, or in any of the nucleotide sequence shown in FIG. 15 (SEQ ID NO: 28) and particularly the coding regions thereof, or a sequence which is degenerately equivalent thereto, or the complement of either.

A distinctive sequence in this context is a sequence derived from the trout bactenecin sequences provided herein, capable of hybridising selectively or specifically to the nucleotide sequence of SEQ ID NO: 1 or 20, or FIG. 15 (SEQ ID NO: 28), and preferably to the coding sequences thereof, in a heterogeneous preparation of nucleic acid, e.g. a preparation of genomic DNA, cDNA or RNA. Such molecules can be used to identify functionally related sequences, e.g. other cathelicidin gene sequences, in nucleic acid preparations from rainbow trout, other piscine species, or any other target species.

The distinctive sequence may comprise 30, 40, 50, 60, 70 80, 90, 100, 150, 200, 250, 300, 400 500 or more contiguous nucleotides of the sequences described herein, or a sequence degenerately equivalent thereto, or the complement of either.

Thus the distinctive sequence may be derived from the open reading frame of SEQ ID NO: 1 or 20, i.e. nucleotides 1 to 647 of SEQ ID NO: 1, or the sequence from nucleotides 5 to 655 of SEQ ID NO: 20, including the TAG stop codon. Additionally or alternatively, the distinctive sequence may be derived in whole or in part from the 3' untranslated region from nucleotide 648 of SEQ ID NO: 1, or any of the non-coding sequences shown in SEQ ID NO: 20 and FIG. 15.

In some embodiments, the distinctive sequence may comprise the whole or part of any one of the cathelin signature sequences (SEQ ID NOs: 6, 8, 25). The distinctive sequence may comprise the whole or part of one or more of SEQ ID NOs: 11, 13, 15, 17, encoding the nonameric repeats from the mature peptide, or of a nucleic acid sequence encoding the nonamer consensus sequence RPG-G/V-GS-X-I/P-G (SEQ ID NO: 19), or any sequence degenerately equivalent to any of the above sequences or the complement thereof.

The sequences referred to above may be modified by addition, substitution, insertion or deletion of one or more nucleotides, but preferably without abolition of ability to hybridize selectively with nucleic acid with the sequence of SEQ ID NO: 1 or 20, or FIG. 15, that is wherein the degree of homology of the oligonucleotide or polynucleotide with one of the sequences given is sufficiently high. The distinctive sequence may have greater than about 40% homology, greater than about 50% homology, greater than about 60% homology, greater than about 70% homology, greater than about 80% homology, greater than about 90% homology or greater than about 95% homology with the whole or part of SEQ ID NO:1 or 20, or the sequence of FIG. 15, for example with the whole or part of SEQ ID NO: 3, 5, 7, 9, 22, 24 or 26, or a sequence degenerately equivalent thereto, or the complement thereof.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5× Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes—1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5°\text{ C.} + 16.6 \text{ Log } [\text{Na}+] + 0.41 \text{ } (\% \text{ } G+C) - 0.63$$
$$(\% \text{ formamide}) - 600/\#\text{bp in duplex}$$

As an illustration of the above formula, using [Na+]=[0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Also provided by the present invention is a method for isolating a nucleic acid encoding a cathelicidin polypeptide or a portion thereof, said method employing an isolated nucleic acid of the present invention.

The methods of the present invention may comprise the steps of:
(a) providing a preparation of nucleic acid from a target organism;
(b) providing a nucleic acid primer or probe as described herein;
(c) contacting said nucleic acid preparation with said primer or probe, and
(d) identifying nucleic acid in said preparation which hybridises with said primer or probe.

The nucleic acid preparation may comprise e.g. genomic DNA, RNA or cDNA. Contact, or hybridisation, between the primer or probe and the nucleic acid preparation may be performed under any suitable conditions. The conditions of the hybridization can be controlled to minimise non-specific binding, and preferably stringent to moderately stringent hybridization conditions are preferred. The skilled person is readily able to design suitable probes, label them and devise suitable conditions for the hybridization reactions, assisted by textbooks such as Sambrook et al (1989) and Ausubel et al (1992), taking into account factors such as oligonucleotide length and base composition, temperature and so on.

Detection and identification of the nucleic acid which hybridises with the primer or probe may be performed by any suitable method, many examples of which are known to the skilled person. For instance, probes may be radioactively, fluorescently or enzymatically labelled.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridized to the DNA fragments on the filter and binding determined. DNA for probing may be prepared from RNA preparations from cells.

Other methods not employing labelling of probe include examination of restriction fragment length polymorphisms, amplification using PCR, RNAse cleavage and allele specific oligonucleotide probing.

For example, the method of identification may involve the polymerase chain reaction, in which case, the method may comprise the steps of:
(a) providing a preparation of nucleic acid from a target organism;
(b) providing a pair of nucleic acid primers, at least one of said primers being a nucleic acid as described herein;
(c) contacting said nucleic acid preparation with said primers under conditions for performance of PCR, and
(d) performing PCR and determining the presence or absence of amplified nucleic acid.

The method may further comprise the step of cloning the amplified nucleic acid. In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

The present invention further comprises methods for producing peptides or polypeptides encoded by nucleic acids identified by the methods set out above. Such methods may comprise the steps of:
(a) isolating a nucleic acid encoding a cathelicidin polypeptide or a portion thereof;
(b) introducing said nucleic acid into a suitable host cell, and
(c) causing or allowing expression of said nucleic acid in said suitable host cell.

Suitable methods for such expression have been described above.

The provision of the novel trout bactenecin peptides and polypeptides enables for the first time the production of antibodies able to bind specifically to these polypeptides, fragments and active portions thereof.

Accordingly, a further aspect of the present invention provides an antibody able to bind specifically to any of the polypeptides of the present invention. Such an antibody may be specific in the sense of being able to distinguish between the polypeptide it is able to bind and other human polypeptides for which it has no or substantially no binding affinity (e.g. a binding affinity of about 1000× worse). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Methods of producing antibodies include immunising a mammal or bird (e.g. human, mouse, rat, rabbit, horse, goat, sheep, monkey or chicken) with the protein or a fragment thereof. Antibodies may be obtained from immunised animals using any of a variety of techniques known in the art, and might be screened, preferably using binding of antibody to antigen of interest. Alternatively, animals may be immunised with DNA encoding the antigen of interest (Donnelly, J. J., Ulmer, J. B., Shiver, J. W. & Liu, M. A. (1997). DNA vaccines. Ann. Rev. Immunol. 15: 617-648).

For instance, Western blotting techniques or immunoprecipitation may be used (Armitage et al, 1992, Nature 357: 80-82). Antibodies may be polyclonal or monoclonal.

Antibodies may be modified in a number of ways. Indeed the term 'antibody' should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the Vl and VH domains of a single antibody; (iv) the dAb fragment (Ward, E. S. et al., Nature 341, 544-546 (1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P Holliger et al. Proc. Natl. Acad. Sci. USA 90 6444-6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of variant polypeptides, and then their encoding genes. Thus, the present invention provides a method of identifying or isolating a cathelicidin peptide, polypeptide or variant thereof (as discussed above), comprising screening candidate polypeptides with a polypeptide comprising the antigen-binding domain of an antibody (for example whole antibody or a fragment thereof) which is able to bind said cathelicidin peptide, polypeptide or variant thereof, or preferably has binding specificity for such a polypeptide. Specific binding members such as antibodies and polypeptides comprising antigen binding domains of antibodies that bind and are preferably specific for a cathelicidin peptide, polypeptide or mutant or derivative thereof represent further aspects of the present invention, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases.

The polypeptides or peptides of the present invention may be used in therapeutic applications. For example, peptides or polypeptides with anti-microbial activity may be useful in the treatment of conditions caused by microbes, e.g. fungal or bacterial infections. For example, some cathelicidins have been shown to be active against a number of bacterial strains, including drug resistant strains, such as *E. coli, Salmonella* enteritides, *Acinetobacter baumannii, Pseudomonas aeruginosa, Klebsiella pneumoniae, Serratia marcescens, Burkholderia cepacia, Staphylococcus aureus* (MRSA—i.e. methicillin resistant), *Staphylococcus epidermidis, Enterococcus faecalis* (VREF—i.e. vancomycin resistant) and *Streptococcus agalactiae*, and also against fungi such as *Candida albicans, Candida glabrata* and *Cryptococcus neoformans* (Gennaro, R & Zanetti, M. (2000). Structural features and biological activities of the cathelicidin-derived antimicrobial peptides. *Biopolymers* 55: 31-49). The trout bactenecin molecule may be active against any of the above mentioned species, and other bacteria of the same genera. It may also be active against fish pathogens. For example, it may be active against *Aeromonas, Vibrio, Yersinia, Flexibacter, Pasteurella, Flavobacterium, Renibacterium* or *Piscirickettsia*, for example *Aeromonas salmonicida, Aeromonas hydrophila, Vibrio anguillarum, Vibrio salmonicida, Yersinia ruckeri, Flexibacter maritimus, Pasteurella piscicida, Flavobacterium psychrophilum, Renibacterium salmoninarum*, or *Piscirickettsia salmonis*.

However, many cathelicidins have relatively non-specific mechanisms of action involving interaction with the microbial membrane, rather than with molecules such as proteins which vary more widely between species, and so may also have applications in the treatment of many other conditions mediated by microbes.

Mature cathelicidin peptides have also been suggested to be capable of immunoregulation, neutralisation of bacterial endotoxin and wound healing. For example, the LL-37 peptide derived from human CAP-18 is capable of binding to and neutralising endotoxin (Larrick, J. W. et al. (1994). *J. Immunol.* 152: 231-240), induces histamine release and intracellular calcium mobilisation in mast cells (Niyonsaba, F. et al. (2001). *Eur. J. Immunol.* 31: 1066-1075), and is chemotactic for neutrophils, monocytes, and T cells, but not dendritic cells (Lillard Jr, J. W. et al. (1999). *Proc. Natl. Acad. Sci. USA* 96: 651-656). The neutralising activity against endotoxin has led it being proposed as a potential therapy for gram-negative sepsis.

Porcine PR-39 is capable, inter alia, of upregulating expression of heparan sulphate proteoglycans called syndecans, which are involved in wound repair (Gallo, R. L. et al. (1994). *Proc. Natl. Acad. Sci. USA* 91: 11035-11039) and has numerous other activities, including anti-inflammatory activities such as reducing production of reactive oxygen species, neutrophil adhesion, etc. (for reviews see Zhang, G. L., Ross, C. R. & Blecha, F. (2000). *Vet. Res.* 31: 277-296; Gennaro, R & Zanetti, M. (2000). Structural features and biological activities of the cathelicidin-derived antimicrobial peptides. *Biopolymers* 55: 31-49).

Accordingly in a further aspect, the present invention provides peptides, polypeptides; and nucleic acids as describczd above for use in a method of medical treatment.

In particular, the peptides, polypeptides and nucleic acids may be used for the treatment of a condition caused by a microbe, for modulating the activity of bacterial endotoxin (e.g. in gram-negative sepsis), for immunoragulation (e.g. the treaitment of inflammation), and for stimulating wound healing.

Also provided is the use of such peptides, polypeptides and nucleic acids in the manufacture of a medicament for the treatment of a treatment of a condition caused by a microbe, for modulating the activity of bacterial endotoxin (e.g. in gram-negative sepsis), for immunoregulation (e.g. the treatment of inflammation), and for stimulating wound healing.

The prealent invention further provides pharmaceutical compositions comprising peptides, polypeptides or nucleic acids of the present invention. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes. For administration to fish, the pharmaceutical composition may be formulated for addition to water containing the fish.

Pharmaceutical compositions for oral administration may be in tablet, capsule, powder or liquid form A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a 'prophylactically effective amount' or a 'therapeutically effective amount' (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners, other medical doctors and veterinary surgeons, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Peptides may, for example, be administered by injection, or for example by transdermal delivery, which can be effected according to methods known in the art. Generally, transdermal delivery involves the use of a transdermal "patch" which allows for slow delivery of compound to a selected skin region. Although such patches are generally used to provide systemic delivery of compound, site-directed delivery can be expected to provide increased concentration of compound in selected regions of tissue. Examples of transdermal patch delivery systems are provided by U.S. Pat. No. 4,655,766 (fluid-imbibing osmotically driven system), and U.S. Pat. No. 5,004,610 (rate controlled transdermal delivery system).

Transdermal delivery of peptides may preferably be carried out using iontophoretic methods, such as described in U.S. Pat. No. 5,032,109 (electrolytic transdermal delivery system), and in U.S. Pat. No. 5,314,502 (electrically powered iontophoretic delivery device).

For transdermal delivery, it may be desirable to include permeation enhancing substances, such as fat soluble substances (e.g., aliphatic carboxylic acids, aliphatic alcohols), or water soluble substances (e.g., alkane polyols such as ethylene glycol, 1,3-propanediol, glycerol, propylene glycol, and the like). In addition, as described in U.S. Pat. No. 5,362,497, a "super water-absorbent resin" may be added to transdermal formulations to further enhance transdermal delivery. Examples of such resins include, but are not limited to, polyacrylates, saponified vinyl acetate-acrylic acid ester copolymers, cross-linked polyvinyl alcohol-maleic anhydride copolymers, saponified polyacrylonitrile graft polymers, starch acrylic acid graft polymers, and the like. Such formulations may be provided as occluded dressings to the region of interest, or may be provided in one or more of the transdermal patch configurations described above.

In other treatment methods, the modulators may be given orally or by nasal insufflation, according to methods known in the art. For administration of peptides, it may be desirable to incorporate such peptides into microcapsules suitable for oral or nasal delivery, according to methods known in the art.

Also provided by the present invention is a method of controlling the growth of a population of a microorganism, comprising the step of contacting the population of said microorganism with a peptide or polypeptide comprising a portion having anti-microbial activity according to the present invention. In preferred embodiments, the growth of the microorganism is controlled by killing of some or all of the population of the microorganism. Thus there is also provided a method of killing a microorganism comprising the step of contacting said microorganism with a peptide or polypeptide comprising a portion having anti-microbial activity according to the present invention.

The peptide or polypeptide comprising a portion having anti-microbial activity may be administered to said microorganism or population of microorganisms either in vivo or in vitro.

Thus there is provided a method of treating a microbial infection by administration of a peptide or polypeptide comprising a portion having anti-microbial activity according to the present invention. The organism to be treated may be any organism having an infection of a microbe against which the peptide or polypeptide of the present invention has anti-microbial activity, and may be e.g. a mammal, bird or fish.

Further there is provided a method of disinfecting a surface or object comprising the step of contacting said surface or object with a peptide or polypeptide comprising a portion having anti-microbial activity according to the present invention.

Particular embodiments of the present invention will now be described by reference to the accompanying figures.

FIG. 3 shows the results of a first round PCR screen of phages, with primers specific for IL-1β1 and IL-1β2, to identify those containing IL-1β1 and IL-1β2 genes.

FIG. 4 shows films from two different plates after a second round of screening phage plaque lifts with the radiolabelled IL-1β probe.

FIG. 8 shows the nucleotide (SEQ ID NO: 1) and predicted amino acid sequence (SEQ ID NO: 2) of cDNA clone 6-3.

FIG. 9 shows alignments of trout cathelin signature sequences with those of known cathelicidins. SEQ ID NOS: are provided to right and left of the alignment.

FIG. 10 is a schematic representation of the structure of the trout cathelicidin.

FIG. 11 shows an alignment of the trout cathelicidin mature peptide with mature peptides of known cathelicidins. SEQ ID NOS are listed on the right.

Figure 1:
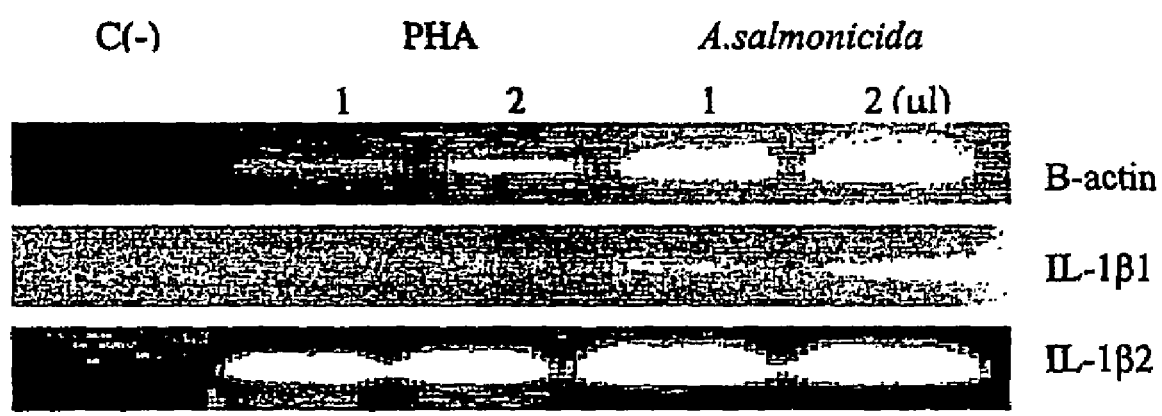
FIG. 1 shows the results of a PCR using primers for β-actin, IL-1β1 and IL-1β2, to test the quality of the cDNA libraries used in the present study.

FIG. 15 shows the genomic sequence (SEQ ID NO: 28) and organisation of the trout cathelicidin gene, showing coding sequence (SEQ ID NO: 29), introns and flanking regions. Non-coding nucleotide sequences are shown in lower case, coding sequences in upper case. Predicted amino acid sequences of the exons are shaded. A putative TATA box is outlined.

MATERIALS AND METHODS

1.1 Libraries

Two different rainbow trout cDNA libraries were constructed using the λZAP Express kit (Stratagene). RNA was extracted from rainbow trout head kidney leukocytes stimulated for 4 hours with phytohemagglutinin (PHA) (Davidson et al., 1999), and from head kidney macrophages isolated from fish challenged with Aeromonas salmonicida (Hardie et al., 1998). RNA was reverse transcribed to cDNA and ligated into the lambda ZAP-CMV XR vector. The construct was packaged in phages (Stratagene) and stored in SM buffer and chloroform at 4° C.

The quality of the libraries was tested by amplifying the genes β-actin, IL-1β1 and IL-1β2 by PCR. β-actin is a housekeeping gene constitutively expressed in all cell types. IL-1β1 and IL-1β2 were used as representative genes induced during immune responses. The primers used for β-actin were forward (5'-ATCGTGGGGCGCCCCAG-GCACC-3' SEQ ID NO: 70) and reverse (5'-CTCCTTAAT-GTCACGCACGATTTC-3' SEQ ID NO: 71), for IL-1β1 were forward F10 (5'-GGATTCACAAGAACTAAGGAC-3' SEQ ID NO: 72) and reverse R3 (5'-CTTAGTTGTG-GCGCTGGATG-3' SEQ ID NO: 73), and for IL-1β2 were forward F4 (5'-ACTACAAAAAGCCAACTACAAACC-3' SEQ ID NO: 74) and reverse R8 (5'-CTCTGCTGCTGGCT-TCAGT-3' SEQ ID NO: 75).

The PCR reaction mix was as follows: 1 or 2 μl of cDNA library, 1 μl 10 mM dNTPs mix, 0.25 μl of 5 units/μl Taq DNA Polymerase, 5 μl 10×NH$_4$ buffer, 1.5 μl 50 mM MgCl$_2$, 2 μl forward primer, 2 μl reverse primer and 35.25 μl of dH$_2$O. The cycling protocol was as follows: initial melting at 94° C. for 5 min, followed by 35 cycles of 94° C. for 1 min, 57° C. for 1 min, 72° C. for 1 min 30 sec, with a final elongation at 72° C. for 10 min. The expected size for the PCR products was ~500 bp for β-actin, 843 bp for IL-1β1, and 323 bp for IL-1β2.

1.2 Preparation of Host Cells

A streak of a glycerol stock of the host bacteria XL-1 Blue MRF' strain (Stratagene) was grown overnight at 37° C. on LB-agar petri dishes (10 g NaCl, 10 g tryptone, 5 g yeast extract, 20 g agar pH 7 in 1 L of dH$_2$O) supplemented with 12.5 μg/ml of tetracycline (Sigma). A single colony was then grown overnight in 6 ml of LB medium (log NaCl, 10 g tryptone, 5 g yeast extract in 1 L dH$_2$O pH 7) supplemented with 10 mM MgSO$_4$ and 0.2% (w/v) maltose at 30° C. 180 rpm. The cells were centrifuged at 2000 rpm 4° C. for 10 min and the pellet suspended in 6 ml of 10 mM MgSO$_4$.

1.3 Titering the Library

To check the titer of the library, 0.6 ml of cells prepared as in 1.2 were incubated for 15 min at 37° C. with 1 μl of a serial of dilutions of the library glycerol stock ($10^{-1}$, $10^{-2}$, $10^{-3}$). The mix was added to 6.5 ml of melted NZY Top agar (5 g NaCl, 2 g MgSO$_4$.7H$_2$O, 5 g yeast extract, 10 g NZ amine, in 1 L dH$_2$O pH 7.5 plus 0.7% (w/v) agarose), poured onto 150 mm NZY agar plates (5 g NaCl, 2 g MgSO$_4$.7H$_2$O, 5 g yeast extract, 10 g NZ amine, 15 g agar in 1 L dH$_2$O pH 7.5) and incubated at 37° C. until bacterial lysis occurred (approx. 5 h). The plaques were counted and the concentration of pfu (plaque forming unit) calculated.

1.4 Plaque Lifts 0.6 ml of cells prepared as in 1.2 were incubated with 1.5×10$^5$ pfu for 15 min at 37° C. and plated as in 1.3. After 5 h the plates were transferred to 4° C. overnight. A nitrocellulose membrane was placed onto each NZY agar plate for 2 min to allow the transfer of the phage particles to the membrane. Duplicates were made, and those were placed for 4 min onto the agar plates. The membranes were marked with an inked-needle for orientation. The membranes were soaked for 2 min in denaturing solution (1.5M NaCl, 0.5M NaOH), neutralised for 5 min in neutralising solution (1.5M NaCl, 0.5M Tris-HCl pH 8.0), and finally rinsed for 30 sec in 0.2M Tris-HCl pH 7.5 and 2×SSC buffer. The membranes were left to air-dry on Whatman® 3 MM and crosslinked under the UV light to fix the phage DNA to the membranes. The plates were stored at 4° C.

1.5 Preparation of Trout IL-1β Probe

A fragment containing the 3' end of the trout IL-1β coding region was amplified by PCR using primers forward F8 (5'-TCTGAGAACAAGTGC-3' SEQ ID NO: 76) and reverse R3 (5'-CTTAGTTGTGGCGCTGGATG-3' SEQ ID NO: 73), and the PHA-stimulated library as template. The PCR reaction mix was as follows: 3 μl of cDNA library, 1 μl 10 mM dNTPs mix, 0.25 μl of 5 units/μl Taq DNA Polymerase, 5 μl 10×NH$_4$ buffer, 1.5 μl 50 mM MgCl$_2$, 2 μl forward primer, 2 μl reverse primer and 35.25 μl of dH$_2$O. The cycling protocol was as follows: initial melting at 94° C. for 5 min, followed by 35 cycles of 94° C. for 45 sec, 57° C. for 45 sec, 72° C. for 1 min, with a final elongation at 72° C. for 10 min. The expected size for the PCR product was 454 bp. The product was separated in a 0.8% agarose gel. The gel was stained with ethidium bromide in order to visualise the bands to ensure they had the right molecular weight. The PCR product was then extracted from the agarose gel using the QIAGEN gel extraction kit and its concentration diluted to 25 ng/ml in TE buffer. A sample from the extracted DNA was sequenced to confirm that the nucleotide sequence was that of IL-1β.

The IL-1β probe was $^{32}$P-labelled prior to hybridisation, using the DNA labelling kit (-dCTP) Ready To Go (Pharmacia Biotech). The tube of reaction mix contained a translucent pellet composed by dATP, dGTP, dTTP, FPLC pure®Klenow fragment (4-8 units) and random oligodeoxyribonucleotides, primarily 9-mers. The contents of the tube were reconstituted by adding 20 μl of distilled water and kept on ice for 1 h. In the meantime, 50 ng of DNA probe were diluted in 25 μl of TE buffer and denatured by heating for 2-3 min at 95-100° C. The DNA was then left on ice for 2 min and centrifuged briefly before adding it to the reconstituted reaction mix. 5 μl of (α-$^{32}$P)-dCTP (300 Ci/mmol) were added to the mix and incubated at 37° C. for 5-15 min. The probe was then ready to use.

1.6 Hybridising and Radioactive Screening

The membranes obtained in 1.4 were placed in glass cylinders and pre-hybridised in 20 ml of pre-hybridisation buffer (Amersham Pharmacia) for 1 h at 65° C. in rotation. After that time 50 μl of the $^{32}$P-labelled IL-1β probe (see 1.5) were added into the cylinder and incubated in the oven at 55° C. for 4 h in rotation. To decrease the excess of unspecific hybridisation astringent washes with different concentrations of SSC (20×SSC: 3M NaCl, 0.5M NaCitrate pH 7)+SDS (Sigma) were performed at 60° C. as follows: 2× (2×SSC+0.1% SDS for 20 min), 2× (0.2×SSC+0.1% SDS for 20 min), and a final 0.1×SSC+0.1% SDS for 15 min. The membrane was then wrapped in clean film and exposed to a Kodak film into a cassette. The films were developed after 24 h.

1.7 Selecting and Extracting Positive Phages

The developed films of each membrane were placed one on top of its duplicate following the orientation marks. The dots that were present in both films were positives for IL-1β hybridisation, the rest were false positives. The area corresponding to a positive phage was selected and extracted from the agar-plates using the top of a sterile 100 µl tip. Each cylinder of agar was placed in Eppendorf tubes containing 500 µl of SM buffer (for 1 litre: 5.8 g NaCl, 2.0 g MgSO$_4$.7H$_2$O, 50 ml 1M Tris-HCl pH 7.5, 5 ml 2% (w/v) gelatin, H$_2$O to 1 litre)+20 µl of chloroform (Sigma). The tubes were vortexed before incubation overnight at 4° C., to ease the release of phage particles.

1.8 PCR Screening of Positive Phages

The phage mix extracted from areas corresponding to positive dots in the radioactive screening were also screened by PCR to discard any phage mix containing the already known IL-1β1 or IL-1β2 cDNAs. For that purpose the titer of the phage had to be increased.

XL-1 Blue MRF' strain (Stratagene) cells were grown overnight in LB medium at 37° C. at 200 rpm. The following day, the bacteria culture was centrifuged at 1500 rpm for 10 min to pellet the cells, which were resuspended in double the amount of medium used the night before. 150 µl of cell suspension were added to 125 µl of the phage stock in SM buffer (see 1.7) and incubated at 37° C. for 15 min to allow the phages to attach to the cells. The mix was added to a tube containing 2.5 ml of LB medium supplemented with 1 mM MgCl$_2$ and incubated at 37° C. at 200 rpm until total bacterial lysis was achieved (approx. 4-6 h). The mix was incubated with 25 ng of Dnase I (Sigma) for 30 min at 37° C. to digest the bacterial DNA released during the lysis, in order to decrease the viscosity.

2.5 ml of 10 mM Tris-HCl pH 8 was then added and the lysates centrifuged at 2500 rpm for 30 min to pellet debris. The supernatants containing the released phages were placed into fresh tubes with a drop of chloroform and stored at 4° C.

Those supernatants were used as template in a PCR reaction to identify and eliminate phages which contained IL-1β genes. The primers used were forward F4 (5'-CGAAT-TCATGGATTTGAGTCA-3' SEQ ID NO: 77) and reverse R3 (5'-CTTAGTTGTGGCGCTGGATG-3' SEQ ID NO: 73), which are capable of amplifying both IL-1β1 and IL-1β2 genes. The PCR reaction mix was as follows: 5 µl of phage mix, 1.5 µl 10 mM dNTPs mix, 0.125 µl of 5 units/µl Taq DNA Polymerase, 2.5 µl 10×NH$_4$ buffer, 0.75 µl 50 mM MgCl$_2$, 1.5 µl forward primer, 1.5 µl reverse primer and 12.125 µl of dH$_2$O. The cycling protocol was as follows: initial melting at 95° C. for 5 min, followed by 35 cycles of 94° C. for 1 min, 58° C. for 1 min, 72° C. for 1 min 30 sec, with a final elongation at 72° C. for 10 min. The expected size for both PCR products was 784 bp.

1.9 Second Round of Radioactive Screening

The phages that hybridised to the IL-1β probe but gave negative results in the PCR screening, i.e. they did not contain IL-1β1 or IL-1β2 genes, were screened for a second time with the $^{32}$P-labelled IL-1β probe to obtain single clones. The stock phages produced in 1.7 were diluted 1:100 in dH$_2$O and 1 µl of the dilution was added to 200 µl of cells prepared as in 1.2. The mix was incubated at 37° C. for 15 min, added to 1 ml of NZY top agar and poured onto NZY agar petri dishes. The petri dishes were placed at 37° C. until lysis was observed and then transferred to 4° C. Plaque lifts were performed as in 1.4 and the membranes hybridised with the IL-1β probe as described above. Comparison of duplicates allowed the identification of positive phages, which were then extracted from agar as in 1.7.

1.10 Second Round of PCR Screening

The single phages obtained as a result of the second round of radioactive screening were again tested by PCR to ensure that no phages contained the cDNAs for the IL-1β1 or IL-1β2 genes, as described above. An additional PCR reaction was carried out to confirm the presence of the lambda ZAP-CMV XR vector in cases where no amplification of IL-1β1/2 was observed. The primers used were T3 (5'-AATTAACCCTCACTAAAGGG-3'(SEQ ID NO: SEQ ID NO: 78) and T7 (5'-CATTATGCTGAGTGATATCCCG-3' SEQ ID NO: 79). The PCR reaction mix was as follows: 5 µl of phage mix, 1.5 µl 10 mM dNTPs mix, 0.125 µl of 5 units/µl Taq DNA Polymerase, 2.5 µl 10×NH$_4$ buffer, 0.75 µl 50 mM MgCl$_2$, 1.5 µl forward primer, 1.5 µl reverse primer and 12.125 µl of dH$_2$O. The cycling protocol was as follows: initial melting at 94° C. for 4 min, followed by 10 cycles of 94° C. for 1 min, 62° C. for 1 min, 68° C. for 15 min, followed by 22 cycles of 94° C. for 40 sec, 62° C. for 40 sec, 68° C. for 15 min+20 sec/cycle, with a final elongation at 68° C. for 10 min. The extremely long extension times were needed because the Lambda ZAP-CMV XR vector can insert sequences up to 10 Kb long.

Thus clones negative for IL-1β1/2 but positive for the vector contained an insert in the vector, which was not IL-1β1/2 cDNA.

1.11 Excision

To analyse and sequence the DNA inserted in the Lambda ZAP-CMV XR vector, the fragment has to be excised from the vector as a phagemid. The ExAssist helper phage is used with XLOLR strain to efficiently excise the pCMVScript EX phagemid vector from the Lambda ZAP-CMV XR vector. Only the excised phagemid will replicate in the host since the ExAssist helper phage has a mutation that prevents replication in XLOLR cells.

XL-1 Blue MRF cells were grown overnight as in 1.2. 200 µl of MRF, 250 µl of phage stock obtained as in 1.9, and 1β1 of ExAssist Helper Phage were incubated at 37° C. for 15 min to allow infection to occur. The mix was then added to 3 ml of NZY broth and incubated at 37° C. overnight to give time to the ExAssist phage to in vivo excise the insert from the lambda vector in MRF cells. The following day, the lambda phage was lysed by heat-treating the culture at 70° C. for 20 min. The phagemid was not affected by this treatment. The culture was then centrifuged for 15 min at 1000 g and the supernatants containing the phagemids collected.

Overnight cultures of XLOLR strain were grown at 30° C., 200 rpm, in NZY broth (1 L: 5 g NaCl, 2 g MgSO$_4$.7H$_2$O, 5 g yeast extract, 10 g NZ amine (casein hydrolysate), pH 7.5). After 24 h, cells were spun down and resuspended in the same volume of 10 mM MgSO$_4$ used for the overnight culture. 10 µl of supernatant were then incubated with 200 µl of freshly prepared XLOLR cells at 37° C. for 15 min to allow infection. This was added to 300 µl of NZY broth and kept at 37° C. for 45 min. 200 µl of the mix were plated on LB plates supplemented with Kanamycin (50 µg/ml) and left overnight at 37° C. Kanamycin would allow selection of clones containing the phagemid. Four clones per plate were further analysed by PCR using universal primers T3 and T7. The PCR mix and cycling protocol were as in 1.10.

These clones were transferred to a 5 ml LB-kanamycin medium and grown overnight at 37° C. The DNA phagemid was extracted from the XLOLR bacteria using a Miniprep kit (QIAGEN). The DNA was diluted to 250 ng/ml and sequenced using an ABI 377 automated sequencer (Applied Biosystems, UK).

1.12 Sequence Analysis

The sequences were analysed for similarity with known sequences using the FASTA (Pearson and Lipman, 1988) and BLAST (Altschul et al., 1990) suite of programs. Direct comparison between DNA sequences and the IL-1β probe were performed using the GAP program (Needlleman and Wunsch, 1970), within the Wisconsin Genetics Computer Group (GCG) Sequence Analysis Software Package (version 9.1, 1997) and multiple sequence alignments were generated using Clustal W (version 1.74, 1997; (Thompson et al., 1994). The analysis of protein structure was performed using the web-based tool SMART (Schultz et al., 2000; Schultz et al., 1998).

1.13 Antimicrobial Peptide Expression Studies

Rainbow trout head kidney leucocytes were obtained by disrupting the head kidney tissue through a 100 μm nylon mesh. After washing, the leucocytes were suspended in L15 medium (Gibco) and stimulated as follows:

(A) LPS time course: Cells were stimulated with 5 μg/ml of *E. coli* 0127:B8 lipopolysaccharide (LPS, Sigma) for different time periods (0, 0.5 h, 1 h, 2 h, 3 h, 4 h).

(B) Transcription/translation inhibition: *Streptomyces* actinomycin D (Sigma) at 100 ng/ml was added to the cells after 3 h of LPS induction (5 μg/ml) to inhibit transcription. Alternatively cycloheximide at 10 μg/ml was added to the cells after 3 h of LPS stimulation (as above) to inhibit translation.

(C) Different inducers: 5 μg/ml of Phytohemagglutinin (PHA, Sigma), 25 ng/ml of Phorbol Myristate Acetate (PMA, Sigma) alone, or in combination with $5\times10^{-7}$M of Calcium Ionophore (Sigma) were added to the cells for 4 h.

At the end of the relevant time period, total RNA was isolated from approximately $2\times10^7$ cells, with RNAzol B (Biogenesis) according to the manufacturer's instructions. The RNA was then reverse transcribed to cDNA and the product used as template in PCRs for the trout cathelicidin gene and β-actin as a positive control. The primers used for the amplification of the cathelicidin gene were fF1 (5'-CATCCTGCTCGCTGTGGCTGTCC-3' SEQ ID NO: 80) and R1 (5'-CCTCCAGAATCGGATGTCTGACC-3' SEQ ID NO: 81), and for the β-actin were forward (5'-ATGGAAGATGAAATCGCC-3' SEQ ID NO: 82) and reverse (5'-TGCCAGATCTTCTCCATG-3' SEQ ID NO: 83). The PCR reaction mix was as follows: 5 μl of phage mix, 1.5 μl 10 mM dNTPs mix, 0.125 μl of 5 units/μl Taq DNA Polymerase, 2.5 μl 10×$NH_4$ buffer, 0.75 μl 50 mM $MgCl_2$, 1.5 μl forward primer, 1.5 μl reverse primer and 12.125 μl of $dH_2O$. The cycling protocol was as follows: initial melting at 94° C. for 4 min, followed by 30 cycles of 94° C. for 45 sec, 60° C. for 45 sec, 72° C. for 1 min, with a final elongation at 72° C. for 10 min. The expected size of the products was 320 bp for the cathelicidin gene and 260 bp for β-actin.

Results

To assess the quality of the cDNA libraries used, three genes were amplified by PCR using the libraries as templates. The first gene, β-actin, is a housekeeping gene constitutively expressed in all cell types. IL-1β1 and IL-1β2 were used as representatives of genes induced during an immune response. The presence of the IL-1β cDNAS in the library suggests that it is likely that cDNAs will be present from other genes induced under similar conditions to IL-1β.

As shown in FIG. 1, β-actin was present in both the library from leukocytes stimulated with PHA and the library obtained from macrophages challenged with the fish pathogen *Aeromonas salmonicida*. IL-1β1 and IL-1β2 cDNAs were also amplified from both libraries.

The PHA library was selected to continue with the study. Its titer was determined to be $1.45\times10^8$ pfu/ml.

2.1 First Round Screening with IL-1β Probe

Figure 2:
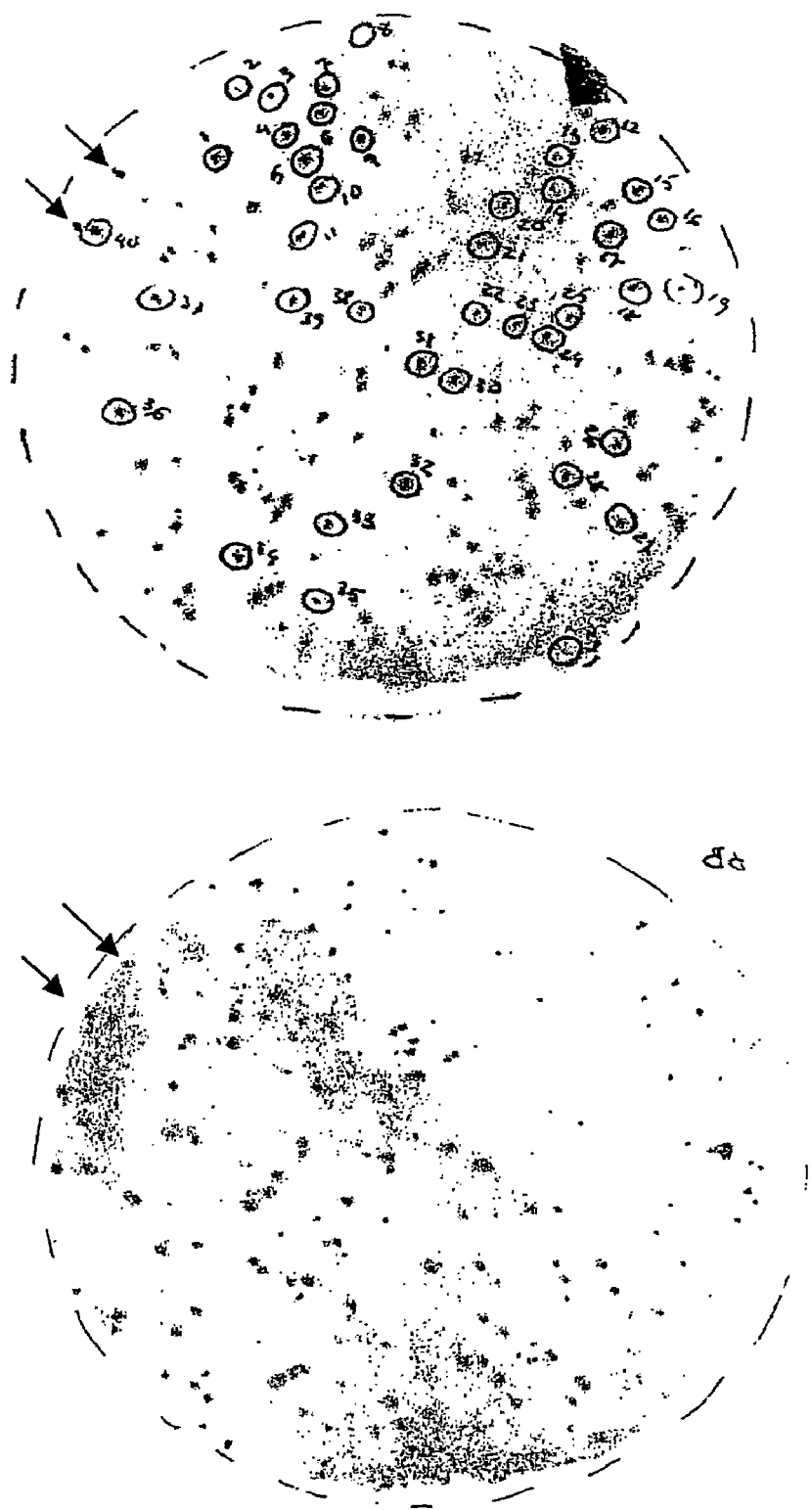
FIG. 2 shows radiographic films of duplicate phage plaque lift membranes from one plate, after hybridisation of the membranes with a radiolabelled IL-1β probe.

A total of 6 plates (14 cm Ø) were analysed. Two duplicate membranes were obtained per plate to distinguish between positives and false positives after the hybridisation. Once the films were developed, the comparison of the duplicate films following the orientation marks revealed approximately 160 positive dots per plate. FIG. 2 shows an example of duplicate films from a single plate after hybridising with the IL-1β probe. The arrows show the orientation marks, while some of the positive clones are indicated by circles. This indicates that approximately it of the phages in the stock library were hybridising to the IL-1β probe at the conditions set for the experiment.

Due to the high total of positive phages (960), only plate number one was used in the following steps. The areas from the agar plates corresponding to positive dots on the films were extracted from the plates and kept in SM buffer and chloroform.

2.2 First Round PCR Screening

To make sure that the selected areas did not contain IL-1β1 or IL-1β2, a sample of the phage stock in SM buffer (see 2.1) was amplified and lysed to be able to perform a PCR for the above-mentioned genes. Since the number of positives per plate was very high only 38 phage stocks were analysed.

From the total of 38 phage stocks, 21 gave positive results in the PCR for IL-1β1/2 using primers F4/R3 (FIG. 3) and were consequently discarded. This value indicated that approximately 55% of the phages that hybridised to the IL-1β probe carried the IL-1β1 or IL-1β2 cDNAs.

2.3 Second Round Screening with the IL-1β Probe

The second round was performed to allow isolation of individual phages. A $10^{-2}$ dilution of the stocks kept in SM buffer (see 2.1) gave a reasonable number of plaques per plate but separated enough to avoid contamination when extracting the phages from the agar. Only 10 of the stocks extracted from the areas corresponding to positive dots in the films (see 2.1) and negative for IL-1β1/IL-1β2 PCR (see 2.2) were screened in the second round. These stocks were 6, 7, 9, 10, 12, 14, 19, 20, 22, and 24, all from plate number 1. The second round was performed in small petri dishes since a high number of positives was not required. Duplicates were not needed on this occasion because it was easy to see if the dots corresponded to a plaque or not since the number of plaques per plate was low. A total of 79 positive phages were observed. Examples of films from two plates after the second round of screening are shown in FIG. 4. Positive clones are indicated by dots.

2.4 Second Round PCR Screening

Figure 5:
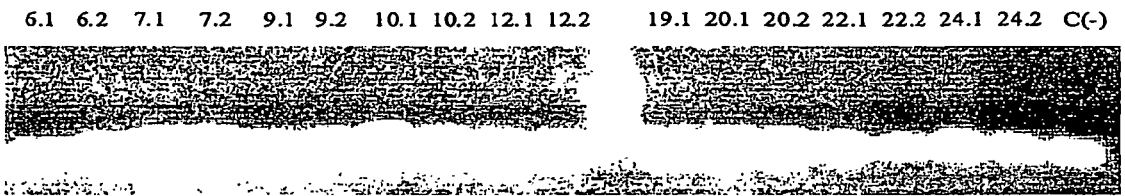
FIG. 5 shows a second round PCR screen of phages to identify any containing IL-1β1 and IL-1β2 genes.

The positive phages obtained in 2.3 were extracted from the agar plate and kept in SM buffer and chloroform and their lysates analysed for the presence of IL-1β1/IL-1β2 by PCR as in the first round. This time none of the plaques was amplified in the PCR, indicating that the cDNA contained in each phage was similar to IL-1β because it hybridised to the IL-1β probe, but that the inserted sequence was not the IL-1β1 or IL-1β2 cDNA since it was not amplified in the PCR with specific primers for IL-1β1/2 (FIG. 5).

Figure 6:
FIG. 6 shows PCR amplification of phage inserts using primers T3 and T7 specific for flanking phage sequences, to confirm the presence of phage DNA.

To make sure that the negative results in the PCR for IL-1β1/2 were not due to the absence of phage DNA, resulting from problems during phage extraction, amplification or lysis, another PCR was performed (FIG. 6) using universal primers T3 and T7, which code for sequences flanking the insertion site in the lambda ZAP-CMV XR vector. Bands were amplified for almost all the samples, indicating the presence of phage vector having cDNA inserts not corresponding to the known IL-1β genes.

2.5 Excision

Figure 7:
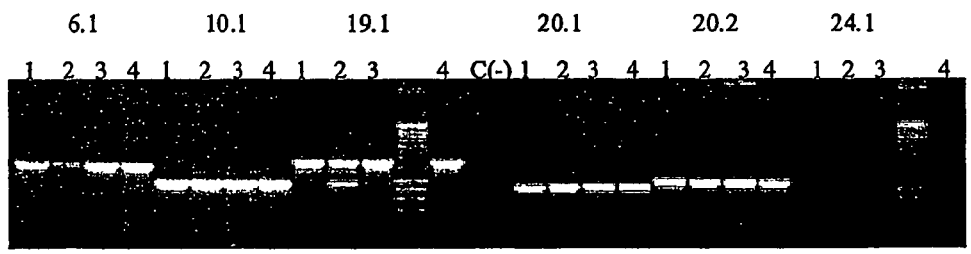
FIG. 7 shows PCR amplification of phage inserts using primers T3 and T7 specific for flanking phage sequences, to analyse the size of the inserts.

The insert in the phages was excised and cloned as a phagemid. In this form the phagemid is capable of infecting and multiplying in XLOLR cells. Only cells containing the phagemid grow on agar plates under kanamycin selection. Four clones per plate were analysed by PCR using the universal primers T3 and T7, present in the phagemid sequence, to evaluate the size of the insert present in the phagemid (FIG. 7).

2.6 Sequence Analysis

The DNA phagemid was extracted from the XLOLR cells and sequenced. The nucleotide sequences and their translations, in the three different reading frames, were compared to other sequences present in the database to be identified. The sequences obtained were aligned to the IL-1β probe sequence and the region that best aligned was compared for nucleotide identity. The range of values obtained fluctuated between 32% and 44%, with the exception of a truncated form of the IL-1β1 gene found that had a higher identity (98%).

2.7 Trout Antimicrobial Peptide (Trout Bactenecin)

Of the 41 clones sequenced, one (designated clone 6-3) had the sequence shown in FIG. 8. A FASTA search indicated that the sequence belonged to the cathelicidin family. This is believed to be the first example of a non-mammalian member of this family which is known to include porcine, ovine, bovine, caprine, murine and human members.

The total length of the sequenced clone was 833 bp, having an incomplete 5' end, frequent in genes cloned from libraries, a 3' UTR containing a polyadenylation site at position +793, and an 18 bp long polyA tail. The clone contains an incomplete open reading frame coding for a 214 amino acid prepropeptide. The first 20 amino acids are characteristic of a signal peptide, indicating that only a small amount of open reading frame is missing from this clone.

The propeptide is believed to begin at residue $Q_{21}$ and contains two cathelin signature sequences (28-44, 75-97; SEQ ID NOs: 6 and 8). FIG. 9 shows alignments of the cathelin signature sequences with those from the following known cathelicidins:

| Sequence | Source |
|---|---|
| PR-39 | porcine PR-39 |
| CATHELIN | porcine Cathelin |
| FALL-39 | human |
| PF2 | porcine Prophenin 2 |
| PG1 | porcine Protegrin 1 |
| PMAP-23 | porcine Myeloid Antibacterial Peptide 23 |
| PMAP-36 | porcine Myeloid Antibacterial Peptide 26 |
| BAC1B | bovine Bactenecin 1 |
| SMAP-29 | sheep Myeloid Antibacterial Peptide 29 |
| BAC7S | sheep Bactenecin 7 |
| BAC11S | sheep Bactenecin 11 |
| BAC6S | sheep Bactenecin 6 |
| BAC5B | bovine Bactenecin 5 |
| INDOL | bovine Indolicidin |
| CATH1 | Cathelin 1 |
| CRAMP | murine Cathelin Related AntiMicrobial Peptide |
| CAP-18 | human |
| BAC-M | murine Bactenecin |
| P15A | rabbit |

The propeptide is further predicted to contain two disulfide bonds linking cysteine residues at positions 82-93 and 104-128. These are illustrated schematically in FIG. 10. The disulphide bonds may impose structural constraints to the molecule. The propeptide of cathelicidins is normally cleaved by elastase, C-terminal of a valine residue, to yield the active mature peptide. $Val_{127}$ aligned with other valine residues from other known peptides of the same family but cleavage in this position would require breaking the disulfide bond between residues 104 and 128 to produce a free mature peptide. Therefore $Val_{148}$ is more likely to be the elastase cleavage site. The propeptide region was found to share up to 29% amino acid similarity with that of other mammalian members of the cathelicidin family.

The mature peptide is therefore predicted to begin at Arg149 and to be 66 amino acids in length. An alignment of the predicted trout cathelicidin mature peptide with mature peptides of other cathelicidins is shown in FIG. 11.

The trout peptide has characteristics of more than one of the 5 subgroups of the cathelicidin family. It has both an internal disulphide bond, characteristic of the dodecapeptide family, and four tandem repeats of a proline- and arginine-rich nonamer sequence (RPG-G/v-GS-X-I/p-G SEQ ID NO: 19) characteristic of the group of the Proline and Arginine Rich peptides (pig prophenins and bovine and sheep bactenecins). As a result, the trout cathelicidin has been classified with the Proline and Arginine Rich peptides, and designated trout bactenecin.

2.8 Sequencing of Full Length ORF

The 5' end of the cDNA was obtained by 5' RACER PCR with a GeneRacer™ kit (Invitrogen Corp. Cat. No. L1500-01). The cDNA template was derived from mRNA extracted from head kidney leucocytes obtained from trout stimulated by intraperitoneal injection with a bacterial CpG oligodinucleotide. The forward primers used were those supplied with the kit, whilst the reverse primers were ACAATTTTTGCCTCTGGAGCATATTCT SEQ ID NO: 84 (for first PCR) and CACAAACAAATGTAGACAGGT-CAGTGTT SEQ ID NO: 85 (for nest PCR). The full length sequence obtained is shown as SEQ ID NO: 20, with predicted amino acid sequence as SEQ ID NO: 21. These sequences show single nucleotide polymorphisms identified in the ORF.

2.9 Sequencing of Genomic DNA

The genomic sequence was obtained by GenomeWalker PCR with a Universal GenomeWalker™ kit (CLONTECH Inc. Cat. No. K1807-1). The DNA template was extracted from rainbow trout head kidney. The forward primers were those supplied with the kit, and the reverse primers were the same as those used in 5' RACER PCR (see above). The sequence obtained is shown as FIG. 15.

The gene is shown to have 4 exons/3 introns, and as predicted from the known mammalian sequences, the predicted functional peptide is completely within exon 4. The 5' flanking (possible promoter) sequence contains a predicted TATA box.

2.10 Expression Studies

Figure 12:
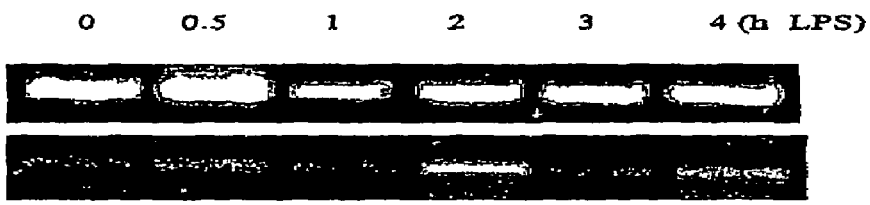
FIG. 12 shows RT-PCR analysis of β-actin and trout cathelicidin expression in trout head kidney leukocytes stimulated with LPS.

To study how the expression of the trout bactenecin gene is regulated, a time course was performed. Trout head kidney total leukocytes were isolated from a single fish and stimulated with 5 μg/ml of LPS. RT-PCR using primers specific for the trout bactenecin gene was performed on cDNA prepared from the stimulated cells (paragraph 1.13), revealing maximum expression of the gene after 2 h of LPS addition and a rapid decrease thereafter (see FIG. 12). This indicated a very tight regulation and rapid degradation of the mRNA.

Figure 13:
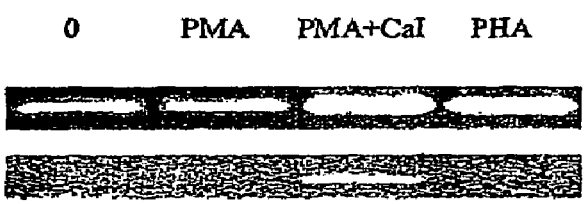
FIG. 13 shows RT-PCR analysis of β-actin and trout cathelicidin expression in trout head kidney leukocytes stimulated with phorbol myristate acetate, phorbol myristate acetate plus calcium ionophore, or phytohemagglutinin.

Phorbol myristate acetate (PMA), PMA+calcium ionophore (PMA+CaI), and phytophemagglutinin (PHA) were also tested for their ability to induce the trout bactenecin expression in leucocytes (FIG. 13). The results showed that after 4 h of induction only PMA+calcium ionophore induced expression. This was interesting since expression after 4 h was not detected with LPS in previous experiments.

To study this further, experiments were performed to study the effects on head kidney total leukocytes stimulated with LPS of inhibiting transcription with actinomycin D (Act D) and translation with cycloheximide (CHX).

Figure 14:
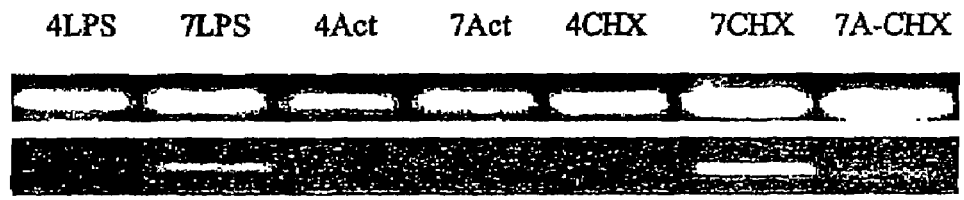
FIG. 14 shows the effects of actinomycin D and cycloheximide on expression of β-actin and trout cathelicidin in trout head kidney leukocytes stimulated with LPS.

Results are shown in FIG. 14. Lanes are marked as follows: 4LPS—4 h incubation with LPS; 7LPS—7 h incubation with LPS. For treatment with ActD and/or CHX, the following was added to the cells after 3 h of LPS stimulation: 4Act—actinomycin for 1 h; 7Act—actinomycin for 4 h; 4CHX—cycloheximide for 1 h; 7CHX—cycloheximide for 4 h; 7A-CHX—actinomycin and an hour later cycloheximide for 3 h. The top gel represents the β-actin control, and the bottom gel the trout bactenecin.

In this case, the maximum expression after LPS stimulation was detected after 7 h. So according to the results from the LPS time course there might be two peaks of expression, one very early only after 2 h of LPS addition non-detectable in this experiment, and a second one detectable after 7 h of LPS stimulation.

The addition of actinomycin D 3 h after the LPS stimulation inhibited completely the expression of the trout bactenecin. This indicated that the transcript observed after 7 h of stimulation with LPS was newly transcribed, which was expected since no expression was observed at 4 h LPS. Cycloheximide, a translation inhibitor, did not induce a superinduction of the bactenecin gene, suggesting that no labile repressors were involved in the regulation of the bactenecin expression. When transcription and translation were both inhibited, a rapid decrease in expression was observed indicating that the bactenecin expression depends mainly on newly transcribed mRNA and that once it is synthesised it is easily degradable. The low expression observed could be due to a slight stabilisation of the mRNA due to a lack of synthesis of the enzymes involved in the degradation of mRNA.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

REFERENCES

Zanetti, M., Gennaro, R., and Romeo, D. (1995). Cathelicidins: a novel protein family with a common proregion and a variable C-terminal antimicrobial domain. *FEBS letters*, 374: 1-5.

Frank, R. W., Gennaro, R., Schneider, K., Przybylski, M., and Romeo, D. (1990). Amino acid sequences of two proline-rich bactenecins. *The Journal of Biological Chemistry*, 265(31): 18871-18874.

Harwig, S. S. L., Kokryakov, V. N., Swiderek, K. M., Aleshina, G. M., Zhao, C., and Lehrer, I. R. (1995). Prophenin-1, an exceptionally proline-rich antimicrobial peptide from porcine leukocytes. *FEBS Letters*, 362: 65-69.

Gennaro, R., Skerlavaj, B., and Romeo, D. (1989) Purification, composition and activity of two bactenecins, antibacterial peptides of bovine neutrophils. *Infect Immun*, 57: 3142-3146.

Genarro, R, Scocchi, M., Merluzzi, L., and Zanetti, M. (1998) Biological characterization of a novel mammalian antimicrobial peptide. *Biochimica et Biophysica Acta*, 1425: 361-368.

Davidson, J., Smith, T., and Martin, S. A. M. (1999). Cloning and sequence analysis of rainbow trout LMP2 cDNA and differential expression of the mRNA. *Fish & Shellfish Immunology*, 9: 621-632.

Hardie, L. J., Laing, K., J, Daniels, G., D, Grabowski, P. S., Cunningham, C., and Secombes, C. J. (1998). Isolation of the first piscine transforming growth factor beta gene. Analysis reveals tissue specific expression and a potential regulatory sequence in rainbow trout (*Oncorhynchus mykiss*). *Cytokine*, 10: 555-563.

Pearson, W. R., and Lipman, D. I. (1988). Improved tools for biological sequence comparison. *Proc Natl Acad Sci USA*, 85: 2444-2448.

Altschul, S. F., Gish, W., Miller, W., Myers, E., and Lipman, D. J. (1990). Best local alignment search tool. *J Mol Biol*, 215: 403-410.

Needlleman, S. B., and Wunsch, C. D. (1970). A general method applicable to the search for similarities in the amino acid sequence of two proteins. *J Mol Biol*, 48: 443-453.

Thompson, S. D., Higgins, D. G., and Gibson, T. J. (1994). Clustal W: improving the sensibility of progressive multiple sequence alignment through sequence weighting, position-specific gap penalties and weight matrix choice. *Nucleic Acids Res*, 22: 4673-4680.

Schultz, J., Copley, R. R., Doerks, T., Ponting, C. P., and Bork, P. (2000). SMART, a web-based tool for the study of genetically mobile domains. *Nucleic Acids Res.*, 28 (1): 231-234.

Schultz, J., Milpetz, F., Bork, P., and Ponting, C. P. (1998). SMART, a simple modular architecture research tool: identification of signaling domains. *Proc. Natl. Acad. Sci. USA*, 95 (11): 5857-5864.

The invention claimed is:

1. An isolated polypeptide having anti-microbial activity, comprising at least two repeats of the amino acid sequence RPG-G/V-GS-X-I/P-G (SEQ ID NO: 19), said polypeptide optionally comprising a pair of cysteine residues capable of forming an internal disulphide bond.

2. A polypeptide according to claim 1, comprising three or four repeats of the amino acid sequence RPG-G/V-GS-X-I/P-G (SEQ ID NO: 19).

3. A polypeptide according to claim 1, wherein one or more of said repeats has the amino acid sequence of SEQ ID NOs: 12, 14, 16 or 18.

4. A polypeptide according to claim 3, comprising each of SEQ ID NOs: 12, 14, 16 and 18.

5. A polypeptide according to claim 1 further comprising a pair of cysteine residues capable of forming an internal disulphide bridge.

6. An isolated polypeptide according to claim 1 said polypeptide having anti-fungal or anti-bacterial activity.

7. A polypeptide according to claim 1, comprising an amino acid sequence as set out in SEQ ID NO: 10 or 27, or a sequence having greater than about 40% identity therewith, said polypeptide comprising at least two repeats of the amino acid sequence RPG-G/V-GS-X-T/P-G (SEQ ID NO: 19).

8. A polypeptide comprising a portion having anti-microbial activity as described in claim 1, and a propeptide portion cleavable from the portion having anti-microbial activity by a protease.

9. A polypeptide according to claim 8, wherein the propeptide portion comprises at least one cathelin signature sequence.

10. A polypeptide according to claim 9, wherein the cathelin signature sequence comprises SEQ ID NO: 6, 8 or 25.

11. A polypeptide according to claim 10, wherein the propeptide portion comprises two cathelin signature sequences each independently selected from the group consisting of SEQ ID NOs: 6, 8 and 25.

12. A polypeptide according to claim 8, wherein the propeptide portion comprises at least one pair of cysteine residues capable of forming an internal disulphide bridge.

13. A polypeptide according to claim 8, wherein the protease is elastase.

14. A polypeptide according to claim 8, wherein the propeptide portion comprises an amino acid sequence as set out in SEQ ID NO: 4 or 23, or a sequence having greater than about 30% identity therewith.

15. A polypeptide according to claim 14, comprising an amino acid sequence as set out in SEQ ID NO: 2 or 21, or a sequence having greater than about 40% identity with SEQ ID NOS: 2 or 21, said sequence comprising at least two repeats of the amino acid sequence RPG-G/V-GS-X-I/P-G (SEQ ID NO: 19).

16. A polypeptide according to claim 2, wherein one or more of said repeats has the amino acid sequence of SEQ ID NOs: 12, 14, 16 or 18.

17. A polypeptide according to claim 3, having anti-fungal or anti-bacterial activity.

18. A polypeptide according to claim 4, having anti-fungal or anti-bacterial activity.

19. A polypeptide according to claim 10, wherein the propeptide portion comprises at least one pair of cysteine residues capable of forming an internal disulphide bridge.

20. A polypeptide according to claim 11, wherein the propeptide portion comprises at least one pair of cysteine residues capable of forming an internal disulphide bridge.

21. A method for the treatment of a condition caused by a microbe, comprising administration of a composition comprising the polypeptide of claim 6, said administration being effective to modulate a process selected from the group consisting of inflammation, and wound healing.

22. The method of claim 21, wherein said composition is formulated for addition to water containing fish.

23. The method of claim 22, wherein said composition is effective to inhibit inflammation.

24. The method of claim 22, wherein said composition is effective to stimulate wound healing.

25. A polypeptide according to claim 7, comprising an amino acid sequence having at least 40% identity with the sequences of SEQ ID NOS: 10 or 27, said sequence comprising at least two repeats of the amino acid sequence RPG-G/V-GS-X-I/P-G (SEQ ID NO: 19).

26. A polypeptide according to claim 14, wherein the propeptide portion comprises an amino acid sequence having at least 40% identity with the sequences of SEQ ID NOS: 4 or 23.

27. A polypeptide according to claim 14, comprising an amino acid sequence having at least 40% identity with SEQ ID NOS: 2 or 21, said sequence comprising at least two repeats of the amino acid sequence RPG-G/V-GS-X-I/P-G (SEQ ID NO: 19).

* * * * *